(12) United States Patent
Lancaster et al.

(10) Patent No.: US 10,982,284 B2
(45) Date of Patent: Apr. 20, 2021

(54) COMPOSITIONS AND METHODS APC, CREB, AND BAD PATHWAYS TO ASSESS AND AFFECT CANCER

(75) Inventors: Johnathan M. Lancaster, Tampa, FL (US); Yin Xiong, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 14/003,147

(22) PCT Filed: Mar. 5, 2012

(86) PCT No.: PCT/US2012/027737
§ 371 (c)(1),
(2), (4) Date: Sep. 4, 2013

(87) PCT Pub. No.: WO2012/122106
PCT Pub. Date: Sep. 13, 2012

(65) Prior Publication Data
US 2013/0344168 A1 Dec. 26, 2013

Related U.S. Application Data

(60) Provisional application No. 61/464,444, filed on Mar. 4, 2011.

(51) Int. Cl.
*C12Q 1/6886* (2018.01)
*G01N 33/50* (2006.01)
(Continued)

(52) U.S. Cl.
CPC .......... *C12Q 1/6886* (2013.01); *A61K 31/00* (2013.01); *G01N 33/5023* (2013.01); *G01N 33/57449* (2013.01)

(58) Field of Classification Search
CPC ............ C12Q 1/6886; C12Q 2600/106; C12Q 2600/158; G01N 33/5023; G01N 33/57449
See application file for complete search history.

(56) References Cited

U.S. PATENT DOCUMENTS

2009/0186024 A1  7/2009  Nevins
2010/0216660 A1  8/2010  Nikolsky

FOREIGN PATENT DOCUMENTS

WO     2012116328     2/2012

OTHER PUBLICATIONS

Sakamoto, K.M. and Frank, D.A. Clinical Cancer Research 15(8):2583 (Apr. 2009).*

(Continued)

*Primary Examiner* — Diana B Johannsen
(74) *Attorney, Agent, or Firm* — Pabst Patent Group LLP

(57) ABSTRACT

Disclosed are compositions and methods for assessing the apoptosis and survival BAD phosphorylation pathway (BAD pathway); and/or (2) the cell cycle role of APC in cell cycle regulation pathway (APC pathway); and/or (3) the transcription CREB pathway (CREB pathway) and for using these pathways to assess, treat, monitor, prognose, diagnose, etc. subjects with cancer. Also disclosed are compositions and methods for identifying molecular pathways that are common to one or more chemotherapeutic agents for the treatment of an oncological disorder, for screening for compounds or agents that can be used to treat ovarian cancer, and for selecting for compounds or agents that can enhance the cytotoxic response of cisplatin, carboplatin, and/or paclitaxel against a cancer cell, such as an ovarian cancer cell or cell line.

2 Claims, 11 Drawing Sheets

(51) Int. Cl.
    G01N 33/574    (2006.01)
    A61K 31/00     (2006.01)

(56) References Cited

OTHER PUBLICATIONS

Aoki, K. and Taketo, M.M. Journal of Cell Science 120(19):3327 (2007).*
Li, B.X. and Xiao, X. ChemBioChem 10:2721 (Oct. 6, 2009).*
Aggarwal, S. et al. Cancer Research 68(4):981 (Feb. 2008).*
Crijns, A.P.G. et al. PLoS Medicine 6(2):e1000024 (Feb. 2009).*
Crijns, A.P.G. et al. PLoS Medicine 6(2):1000024 "Supplemental Table S3" (Feb. 2009).*
Ait-Si-Ali, et al., "Histone acetyltransferase activity of CBP is controlled by cycle-dependent kinases and oncoprotein E1A", Nature, 396:184-6 (1998).
Allam, et al., "Cholera toxin triggers apoptosis in human lung cancer cell lines", Cancer Res. 57:2615-8 (1997).
Bannister and Kouzarides, "The CBP co-activator is a histone acetyltransferase", Nature, 384:641-3 (1996).
Bolstad, et al., "A comparison of normalization methods for high density oligonucleotide array data based on variance and bias", Bioinformatics 19:185-93 (2003).
Bonni, et al.,"Cell survival promoted by the RAS-MAPK signaling pathway by transcription-dependent and -independent mechanisms", Science, 286:1358-62 (1999).
Boren, et al., "MicroRNAs and their target messenger RNAs associated with ovarian cancer response to chemotherapy", Gynecol Oncol 113: 249-55 (2009).
Chan, et al., "Prospective randomized trial of docetaxel versus doxorubicin in patients with metastatic breast cancer", J. Clin. Oncol. 17:2341-54 (1999).
Chattopadhyay, et al., "BAD/BCL-[X(L)] heterodimerization leads to bypass of G0/G1 arrest", Oncogene, 20:4507-18 (2001).
Chen, et al., Proliferative genes dominate malignancy-risk gene signature in histologically-normal breast tissue. Breast Cancer Res Treat 119: 335-46 (2010).
Crown, "The platinum agents: a role in breast cancer treatment", Seminars in Oncol. 28:28-37 (2001).
Datta, et al., "Akt phosphorylation of BAD couples survival signals to the cell-intrinsic death machinery", Cell, 91:231-41 (1997).
Datta, et al., "14-3-3 proteins and survival kinases cooperate to inactivate BAD by BH3 domain phosphorylation", Mol Cell, 6:41-51 (2000).
Del Peso, et al., "Interieukin-3-induced phosphorylation of BAD through the protein kinase Akt", Science, 278:687-9 (1997).
Dressman, et al., "An integrated genomic-based approach to individualized treatment of patients with advanced-stage ovarian cancer", J Clin Oncol., 25:517-25 (2007).
Du Bois, et al., "A randomized clinical trial of cisplatin/paclitaxel versus carboplatin/paclitaxel as first-line treatment of ovarian cancer", J Natl Cancer Inst., 95:1320-9 (2003).
Etemadmoghadam, et al., "Integrated genome-wide DNA copy number and expression analysis identifies distinct mechanisms of primary chemoresistance in ovarian carcinomas", Clin Cancer Res., 15:1417-27 (2009).
Fernando, et al., "Breast cancer cell proliferation is inhibited by BAD: regulation of cyclin D1", J Biol Chem., 282:28864-73 (2007).
Gao, et al., "Phosphorylation by Akt1 promotes cytoplasmic localization of Skp2 and impairs APCCdh1-mediated Skp2 destruction", Nat Cell Biol., 11:397-408 (2009).
Garcia-Higuera, et al., "Genomic stability and tumour suppression by the APC/C cofactor Cdh1", Nat Cell Biol., 10:802-11 (2008).
Gonzalez and Montminy, "Cyclic AMP stimulates somatostatin gene transcription by phosphorylation of CREB at serine 133", Cell, 59:675-80 (1989).
Hajra, et al., "Defective apoptosis underlies chemoresistance in ovarian cancer", Adv Exp Med Biol., 622:197-208 (2008).
Harada, et al., "p70S6 kinase signals cell survival as well as growth, inactivating the pro-apoptotic molecule BAD", PNAS, 98:9666-70 (2001).
Holmgreen, et al., Survival activity of Bcl-2 homologs Bcl-w and A1 only partially correlates with their ability to bind pro-apoptotic family members. Cell Death Differ 6:525-32 (1999).
Irizarry, et al., "Antonellis KJ, Scherf U, Speed TP (2003) Exploration, normalization, and summaries of high density oligonucleotide array probe level data", Biostatistics 4: 249-64 (2003).
Iyer, et al., "p300/CBP and cancer", Oncogene, 23:4225-31,(2004).
Jia, et al., "Subcellular distribution and redistribution of Bcl-2 family proteins in human leukemia cells undergoing apoptosis", Blood, 93:2353-9 (1999).
Konishi, et al., "Cdc2 phosphorylation of BAD links the cell cycle to the cell death machinery", Mol Cell, 9:1005-16 (2002).
Kreitman and Pastan, "Recombinant toxins containing human granulocyte-macrophage colony-stimulating factor and either pseudomonas exotoxin or diphtheria toxin kill gastrointestinal cancer and leukemia cells", Blood 90:252-259 (1997).
Lappano and Maggiolini, "G protein-coupled receptors: novel targets for drug discovery in cancer", Nat Rev Drug Discov.,10:47-60 (2011).
Lee, et al., "Inactivating mutations of proapoptotic Bad gene in human colon cancers", Carcinogenesis, 25:1371-6 (2004).
Lizcano, et al., "Regulation of BAD by cAMP-dependent protein kinase is mediated via phosphorylation of a novel site, Ser155", Biochem J., 349:547-57 (2000).
Martin, et al., "Cancer gene therapy by thyroid hormone-mediated expression of toxin genes", Cancer Res., 60:3218-24 (2000).
Mayr and Montminy, "Transcriptional regulation by the phosphorylation-dependent factor CREB", Nat Rev Mol Cell Biol., 2:599-609 (2001).
McGuire, et al., "Cyclophosphamide and cisplatin compared with paclitaxel and cisplatin in patients with stage III and stage IV ovarian cancer", N Engl J Med., 334:1-6 (1996).
Miller, et al., Reporting results of cancer treatment. Cancer 47: 207-14 (1981).
Montopoli, et al., "Metabolic reprogramming" in ovarian cancer cells resistant to cisplatin, Curr Cancer Drug Targets, 11:226-35 (2011).
Nakayama and Nakayama, "Ubiquitin ligases: cell-cycle control and cancer",. Nat Rev Cancer, 6:369-81 (2006).
Neijt, et al., "Exploratory phase III study of paclitaxel and cisplatin versus paclitaxel and carboplatin in advanced ovarian cancer", J Clin Oncol., 18:3084-92 (2000).
Osborne and Coronado-Heinsohn, "Targeting the epidermal growth factor receptor in breast cancer cell lines with a recombinant ligand fusion toxin (DAB389EGF)", Cancer J. Sci. Am. 2:175 (1996).
Ozols, et al., "Phase III trial of carboplatin and paclitaxel compared with cisplatin and paclitaxel in patients with optimally resected stage III ovarian cancer: a Gynecologic Oncology Group study", J Clin Oncol., 21:3194-200 (2003).
Paridaens, et al., "Paclitaxel versus doxorubicin as first-line single-agent chemotherapy for metastatic breast cancer: a European Organization for Research and Treatment of Cancer Randomized Study with cross-over", J. Clin. Oncol., 18:724-33 (2000).
Parker, et al., "Phosphorylation of CREB at Ser-133 induces complex formation with CREB-binding protein via a direct mechanism", Mol Cell Biol., 16:694-703 (1996).
Ranger, et al., "Bad-deficient mice develop diffuse large B cell lymphoma", PNAS, 100:9324-9 (2003).
Roy, et al., "Bad targets the permeability transition pore independent of Bax or Bak to switch between Ca2+-dependent cell survival and death", Mol Cell,33:377-88 (2009).
Rustin, et al., "Use of tumour markers in monitoring the course of ovarian cancer", Ann Oncol., 10 Suppl 1:21-7 (1999).
Rustin, et al., "Defining response of ovarian carcinoma to initial chemotherapy according to serum CA 125", J Clin Oncol 14: 1545-51 (1996).
Searle, et al., "The DNA damage checkpoint and PKA pathways converge on APC substrates and Cdc20 to regulate mitotic progression", Nat Cell Biol., 6:138-45 (2004).

(56) References Cited

OTHER PUBLICATIONS

Siu and Jin, "CREB—a real culprit in oncogenesis", FEBS J, 274:3224-32 (2007).
Smith, et al., "Experimentally derived metastasis gene expression profile predicts recurrence and death in patients with colon cancer", Gastroenterology 138:958-968 (2009).
Song, et al., "Nuclear PTEN regulates the APC-CDH1 tumor-suppressive complex in a phosphatase-independent manner", Cell, 144:187-99 (2011).
Takahashi, et al., "Cyclin A-associated kinase activity is needed for paclitaxel sensitivity", Mol Cancer Ther., 4:1039-46 (2005).
Turnell, et al., "The APC/C and CBP/p300 cooperate to regulate transcription and cell-cycle progression", Nature, 438:690-5 (2005).
Wang, et al., "Alterations of anaphase-promoting complex genes in human colon cancer cells", Oncogene, 22:1486-90 (2003).
Wilson, et al., "Induction of bcl-2 expression by phosphorylated CREB proteins during B-cell activation and rescue from apoptosis", Mol Cell Biol., 16:5546-56 (1996).
Yang, et al., "Bad, a heterodimeric partner for Bcl-XL and Bcl-2, displaces Bax and promotes cell death", Cell, 80:285-91 (1995).
Zachariae, et al., "Control of cyclin ubiquitination by CDK-regulated binding of Hct1 to the anaphase promoting complex", Science, ;282:1721-4 (1998).
Zha, et al., "BH3 domain of BAD is required for heterodimerization with BCL-XL and pro-apoptotic activity", J Biol Chem., ;272:2410-4 (1997).
Zha, et al., "Serine phosphorylation of death agonist BAD in response to survival factor results in binding to 14-3-3 not BCL-X(L)", Cell, 87:619-28 (1996).
Zhang, et al., Genome-wide analysis of cAMP-response element binding protein occupancy, phosphorylation, and target gene activation in human tissues. PNAS, 102:4459-64 (2005).

\* cited by examiner

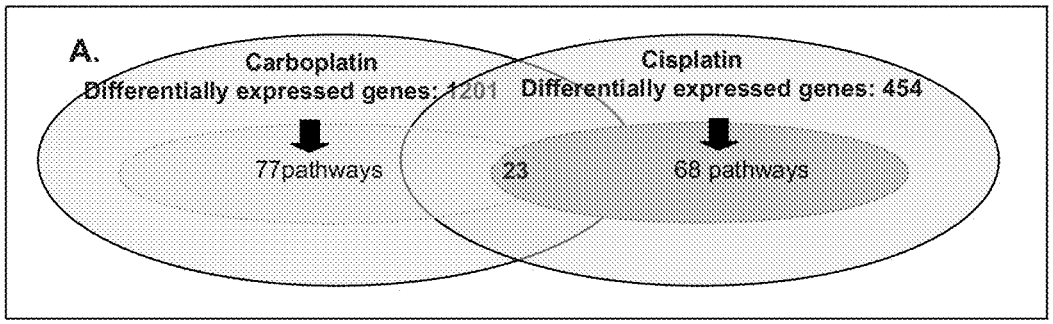

- Apoptosis and survival_BAD phosphorylation
- Apoptosis and survival_HTR1A signaling
- Cell cycle_Role of APC in cell cycle regulation
- Development_ACM2 and ACM4 activation of ERK
- Development_Activation of Erk by ACM1, ACM3 and ACM5
- Development_Activation of ERK by Alpha-1 adrenergic receptors
- Development_Activation of ERK by Kappa-type opioid receptor
- Development_Alpha-2 adrenergic receptor activation of ERK
- Development_Angiotensin activation of ERK
- Development_Angiotensin activation of ERK
- Development_Beta-adrenergic receptors regulation of ERK
- Development_G-Proteins mediated regulation MARK-ERK signaling
- Development_PDGF signaling via MAPK cascades
- Development_Thyroliberin signaling
- Immune response_HTR2A-induced activation of cPLA2
- Immune response_MIF – the neuroendocrine-macrophage connector
- Immune response_Neurotensin-induced activation of IL-8 in colonocytes
- Membrane-bound ESR1: interaction with G-proteins signaling
- Muscle contraction_Regulation of eNOS activity in cardiomyocytes
- Neurophysiological process_Delta-type opioid receptor in the nervous system
- Neurophysiological process_Melatonin signaling
- Signal transduction_Erk Interactions: Inhibition of Erk
- Transcription_CREB pathway

Carboplatin + Paclitaxel Differentially expressed genes: 1049 → 25 pathways

Paclitaxel Differentially expressed genes: 1025 → 64 pathways

Overlap: 2

- Cell cycle_Spindle assembly and chromosome separation
- Transcription_Ligand-Dependent Transcription of Retinoid-Target genes

C.

Carboplatin + Paclitaxel Differentially expressed genes: 1049 → 25 pathways

Carboplatin Differentially expressed genes: 1201 → 77 pathways

Overlap: 8

- Apoptosis and survival_BAD phosphorylation
- Cell cycle_ESR1 regulation of G1/S transition
- Cell cycle_Regulation of G1/S transition (part 1)
- Cell cycle_Role of APC in cell cycle regulation
- Cell cycle_Role of SCF complex in cell cycle regulation
- Cell cycle_Spindle assembly and chromosome separation
- Transcription_CREB pathway
- Translation   Regulation of EIF2 activity

D.

Carboplatin + Paclitaxel Differentially expressed genes: 1049 → 25 pathways

Cisplatin Differentially expressed genes: 454 → 68 pathways

Overlap: 3

- Apoptosis and survival_BAD phosphorylationCell cycle
- Role of APC in cell cycle regulation
- Transcription_CREB pathway FIG. 2B, FIG. 2C, and FIG. 2D

COMPOSITIONS AND METHODS APC, CREB, AND BAD PATHWAYS TO ASSESS AND AFFECT CANCER

CROSS-REFERENCE TO RELATED APPLICATIONS

This application claims benefit of U.S. Provisional Application No. 61/464,444, filed Mar. 4, 2011. Application No. 61/464,444, filed Mar. 4, 2011, is hereby incorporated herein by reference in its entirety.

STATEMENT REGARDING FEDERALLY SPONSORED RESEARCH

This invention was made with government support under Grant R21CA-110499-01A2 awarded by the National Cancer Institute (NCI) and Grant DAMD 17-02-2-0051 awarded by the U.S. Army Medical Research and Materiel Command. The government has certain rights in the invention.

FIELD OF THE INVENTION

The disclosed invention is generally in the field of cancer assessment and treatment and specifically in the area of use of pathways associated with cancer and cancer treatment to assess and treat cancer.

BACKGROUND OF THE INVENTION

The American Cancer Society ranks ovarian cancer (OVCA) as the fifth leading cause of cancer mortality in women, accounting for more deaths than any other gynecologic cancer. In 2010 in the United States alone, approximately 22,000 women had been predicted to be diagnosed with OVCA, with an estimated 14,000 women dying of their disease. (Jemal et al) This high mortality is attributed not only to the advanced stage (III/IV) at diagnosis observed for most patients (Herrin & Thigpen, 1999) but also to limited treatment options available for patients who develop acquired resistance to chemotherapy.

After cytoreductive surgery, most patients with advanced-stage disease receive systemic treatment with a platinum plus/minus taxane-based regimen. Cisplatin and carboplatin have been shown to have similar therapeutic efficacies against ovarian cancer (OVCA), but different toxicity profiles, either alone or in combination with paclitaxel. The molecular basis of OVCA response to each drug, either as single-agents or in combination, remains to be fully delineated.

Clinical trials performed in the 1980s and 1990s established the platinum compounds to be superior to alkylating agents, either alone or in combination with other non-platinum drugs. (Omura et al, 1986) Cisplatin and carboplatin do not differ significantly in their efficacy or effect on survival but do have markedly different side effects. (Ozols et al, 2003) Paclitaxel, a compound extracted from Pacific yew tree bark, has been used as an antineoplastic agent since the 1980s and has been shown to improve OVCA progression-free and overall survival when combined with cisplatin or carboplatin in first-line therapy. (McGuire et al, 1996) Randomized clinical trials comparing the combination of paclitaxel with either cisplatin or with carboplatin in patients with advanced-stage OVCA found no significant differences in efficacy between the two combination treatments, although there was generally an improved tolerability for the carboplatin-containing regimen. (du Bois et al, 2003; Neijt et al, 2000; Ozols et al, 2003) Despite substantial clinical data demonstrating the superiority of platinum-based regimens versus non-platinum regimens, the non-inferiority of carboplatin over cisplatin, and the benefit of paclitaxel combined with platinum-based regimens, the molecular basis to OVCA sensitivity to these drugs remains to be fully characterized.

It would be useful to have ways to assess chemo-resistance and clinical outcome in treated patients and to identify characteristics and targets to overcome chemo-resistance. In the current study, a genomic approach was adopted to characterize unique and common pathways that underlie ovarian cancer response to cancer treatments.

BRIEF SUMMARY OF THE INVENTION

Disclosed are compositions and methods for assessing the apoptosis and survival BAD phosphorylation pathway (BAD pathway); and/or (2) the cell cycle role of APC in cell cycle regulation pathway (APC pathway); and/or (3) the transcription CREB pathway (CREB pathway) and for using these pathways to assess, treat, monitor, prognose, diagnose, etc. subjects with cancer. Also disclosed are compositions and methods for identifying molecular pathways that are common to one or more chemotherapeutic agents for the treatment of an oncological disorder, for screening for compounds or agents that can be used to treat ovarian cancer or colon cancer, and for selecting for compounds or agents that can enhance the cytotoxic response of cisplatin, carboplatin, and/or paclitaxel against a cancer cell, such as an ovarian cancer cell or cell line or colon cancer cell or cell line. In some forms, the disclosed methods can comprise identifying compounds and/or agents that modulate the BAD pathway and/or the APC pathway; and/or the CREB pathway. In some forms, the disclosed methods can comprise method for treating cancer using compounds and/or agents that modulate the BAD pathway and/or the APC pathway; and/or the CREB pathway. Also disclosed are compositions, compounds, and agents identified using the disclosed methods.

Disclosed are methods of assessing a subject with cancer. In some forms, the method comprises determining a CREB pathway gene expression signature score for a cancer sample from the subject, wherein a low CREB pathway gene expression signature score indicates that the subject has greater chance of a positive clinical outcome. A high CREB pathway gene expression signature score indicates that the subject has lower chance of a positive clinical outcome (or a greater chance of a negative clinical outcome). In some forms, the method comprises determining an APC pathway gene expression signature score for a cancer sample from the subject, wherein a high APC pathway gene expression signature score indicates that the subject has greater chance of a positive clinical outcome. A low APC pathway gene expression signature score, or a combination indicates that the subject has lower chance of a positive clinical outcome (or a greater chance of a negative clinical outcome). In some forms, the method comprises determining both a CREB pathway gene expression signature score and an APC pathway gene expression signature score for a cancer sample for a cancer sample from the subject, wherein a low CREB pathway gene expression signature score, a high APC pathway gene expression signature score, or a combination indicates that the subject has greater chance of a positive clinical outcome. A high CREB pathway gene expression signature score, a low APC pathway gene expression signature score, or a combination indicates that the subject has lower chance of a positive clinical outcome (or a greater chance of a negative clinical outcome). In some forms, the method can also comprise determining a BAD pathway gene expression signature score for a cancer sample from the subject, wherein a low BAD pathway gene expression signature score indicates that the subject has greater chance of a positive clinical outcome. A high BAD pathway gene expression signature score indicates that the subject has lower chance of a positive clinical outcome (or a greater chance of a negative clinical outcome). In some forms, the method comprises determining a CREB pathway gene expression signature score for a colon cancer sample from the subject, wherein a high CREB pathway gene expression signature score indicates that the subject with colon cancer has greater chance of a positive clinical outcome. A low CREB pathway gene expression signature score indicates that the subject with colon cancer has lower chance of a positive clinical outcome (or a greater chance of a negative clinical outcome).

Also disclosed are methods of determining the clinical outcome or predicting the clinical outcome of cancer treatment. In some forms, the method comprises determining a CREB pathway gene expression signature score for a cancer sample, where the CREB pathway gene expression signature score indicates the clinical outcome of the treatment on the cancer, where a low CREB pathway gene expression signature score compared to a median CREB pathway gene expression signature score indicates that the subject has greater chance of a positive clinical outcome.

In some forms, the method comprises determining a APC pathway gene expression signature score for a cancer sample, where the APC pathway gene expression signature score indicates the clinical outcome of the treatment on the cancer, where a high APC pathway gene expression signature score compared to a median APC pathway gene expression signature score indicates that the subject has greater chance of a positive clinical outcome.

In some forms, the method comprises determining a CREB pathway gene expression signature score for a colon cancer sample, where the CREB pathway gene expression signature score indicates the clinical outcome of the treatment on the colon cancer, where a high CREB pathway gene expression signature score compared to a median CREB pathway gene expression signature score indicates that the subject with colon cancer has greater chance of a positive clinical outcome.

In some forms, the pathway gene expression signature score can be determined by determining the expression of signature pathway genes, and calculating the pathway gene expression signature score from the expression of signature pathway genes. In some forms, the pathway gene expression signature score can be determined by
$\Sigma w_i x_i$, where $x_i$ represents gene i expression level and $w_i$ is the corresponding weight (loading coefficient) with $\Sigma w_i^2 = 1$. A CREB pathway gene expression signature score above the median value indicates poor clinical outcome to the treatment, a CREB pathway gene expression signature score below the median indicates positive clinical outcome to the treatment, an APC pathway gene expression signature score below the median value indicates poor clinical outcome to the treatment, an APC pathway gene expression signature score above the median indicates positive clinical outcome to the treatment, a BAD pathway gene expression signature score above the median value indicates poor clinical outcome to the treatment, and a BAD pathway gene expression signature score below the median indicates positive clinical outcome to the treatment. A CREB pathway gene expression signature score in colon cancer below the median value indicates poor clinical outcome to the treatment and a CREB pathway gene expression signature score in colon cancer above the median indicates positive clinical outcome to the treatment.

In some forms, the expression of at least 80% of the signature pathway genes can be determined. In some forms, the clinical outcome is chemotherapeutic effect, wherein the chemotherapeutic can be cisplatin, carboplatin, paclitaxel, or a combination. In some forms, the clinical outcome can be survival. In some forms, the cancer can be colon cancer. In some forms, the chance of a positive clinical outcome is greater than the indicated chance of a positive clinical outcome if the cancer exhibited a complete response to chemotherapy. In some forms, the chance of a positive clinical outcome is less than the indicated chance of a positive clinical outcome if the cancer exhibited an incomplete response to chemotherapy.

Also disclosed are methods of treating cancer. In some forms, the method comprises determining a CREB pathway gene expression signature score for a cancer sample from the subject, and administering to the subject an antagonist of the CREB pathway if the cancer sample has a low CREB pathway gene expression signature score. In some forms, the method can further comprise determining an APC pathway gene expression signature score for a cancer sample from the subject, and administering to the subject an agonist of the APC pathway if the cancer sample has a high APC pathway gene expression signature score. In some forms, the method comprises determining an APC pathway gene expression signature score for a cancer sample from the subject, and administering to the subject an agonist of the APC pathway if the cancer sample has a high APC pathway gene expression signature score. In some forms, the method can further comprise determining a CREB pathway gene expression signature score for a cancer sample from the subject, and administering to the subject an antagonist of the CREB pathway if the cancer sample has a low CREB pathway gene expression signature score. In some forms, the method comprises determining a CREB pathway gene expression signature score for a colon cancer sample from the subject, and administering to the subject with colon cancer an antagonist of the CREB pathway if the colon cancer sample has a high CREB pathway gene expression signature score. In some forms, the method can further comprise administering a cancer chemotherapeutic to the subject.

Also disclosed are methods for identifying molecular pathways that are common to one or more chemotherapeutic agents for the treatment of an oncological disorder. In some forms, the method comprises (a) contacting a cancer cell or cancer cell line with the one or more agents and quantifying a dose response effect ($IC_{50}$) for each agent or combination of agents, and, in parallel, (b) determining gene expression for each cell or cell line and agent or combination of agents, (c) evaluating gene expression and chemotherapeutic dose response data for each agent or combination of agents for correlation, and (d) analyzing genes that demonstrate expression and dose response ($IC_{50}$) correlations to identify significantly represented molecular pathways, thereby identifying pathways common to one or more of the agents and cells.

In some forms, the oncological disorder can be one that is sensitive to treatment by cisplatin, carboplatin, paclitaxel, or a combination. In some forms, the oncological disorder can be ovarian cancer. In some forms, the oncological disorder can be colon cancer.

Also disclosed are methods for screening for compounds or agents that can be used to treat ovarian cancer or colon cancer. In some forms, the method comprises testing, identifying, or both compounds, agents, or both that target the apoptosis and survival BAD phosphorylation pathway, the cell cycle role of APC in cell cycle regulation pathway, the transcription CREB pathway, or a combination. In some forms, the compound or agent modulates the function, activity, amount, expression, or a combination of an expression product associated with the apoptosis and survival BAD phosphorylation pathway, the cell cycle role of APC in cell cycle regulation pathway, the transcription CREB pathway, or a combination.

Also disclosed are methods for selecting for compounds or agents that can enhance the cytotoxic response of cisplatin, carboplatin, paclitaxel, or a combination against a cancer cell. In some forms, the method comprises testing, identifying, or both compounds or agents that modulate the apoptosis and survival BAD phosphorylation pathway, the cell cycle role of APC in cell cycle regulation pathway, the transcription CREB pathway, or a combination. In some forms, the compound or agent modulates the function, activity, amount, expression, or a combination of an expression product associated with the apoptosis and survival BAD phosphorylation pathway, the cell cycle role of APC in cell cycle regulation pathway, the transcription CREB pathway, or a combination.

Disclosed are methods for identifying molecular pathways that are common to one or more chemotherapeutic agents for the treatment of an oncological disorder. In some forms, the methods can comprise contacting a cancer cell or cancer cell line with the one or more agents and quantifying a dose response effect ($IC_{50}$) for each agent and/or combination of agents and, in parallel, determining gene expression for each cell or cell line and agent and/or combination of agents. Gene expression and chemotherapeutic dose response data can then be evaluated for each agent and/or combination of agents for correlation (e.g., Pearson's correlation). Genes that demonstrate expression and dose response ($IC_{50}$) correlations can then be analyzed to identify significantly represented molecular pathways wherein pathways common to one or more of the agents and cells can be identified.

Disclosed are methods for screening for compounds or agents that can be used to treat ovarian cancer or colon cancer. In some forms, the methods can comprise testing and identifying compounds and/or agents that target (1) the apoptosis and survival BAD phosphorylation pathway (BAD pathway); and/or (2) the cell cycle role of APC in cell cycle regulation pathway (APC pathway); and/or (3) the transcription CREB pathway (CREB pathway).

Disclosed are methods for selecting for compounds or agents that can enhance the cytotoxic response of cisplatin, carboplatin, and/or paclitaxel against a cancer cell, such as an ovarian cancer cell or cell line or a colon cancer cell or cell line.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 2A-2D are diagrams and lists showing shared biological pathway activation between chemotherapeutic agent treatments. The Pearson correlation test was performed to analyze the relationship between $IC_{50}$ values and gene expression. Genes whose expression highly correlated with the $IC_{50}$ value associated with each drug (P<0.01) were uploaded into the GeneGo MetaCore software to identify significantly represented pathways (P<0.05). A: OVCA cell line sensitivity to carboplatin or cisplatin treatment was associated with 1201 and 454 genes, respectively. Genes associated with OVCA sensitivity to carboplatin and cisplatin were represented in 77 (carboplatin) and 68 (cisplatin) biological pathways. B: OVCA cell line sensitivity to paclitaxel or carboplatin plus paclitaxel treatment was associated with the expression of 1025 and 1049 genes, respectively. Genes associated with OVCA sensitivity were represented in 64 (paclitaxel) and 25 (carboplatin plus paclitaxel) biological pathways. C: OVCA cell line sensitivity to carboplatin plus paclitaxel treatment or carboplatin was associated with the expression of 1049 and 1201 genes, respectively. Genes associated with OVCA sensitivity were represented in 25 (carboplatin plus paclitaxel) and 77 (carboplatin) biological pathways. D: OVCA cell line sensitivity to carboplatin plus paclitaxel treatment or cisplatin treatment was associated with the expression of 1049 and 454 genes, respectively. Genes associated with OVCA sensitivity were represented in 25 (carboplatin plus paclitaxel) and 68 (cisplatin) biological pathways.

In FIG. 4A, the curve to the right and bottom is high CREB and the curve to the left and top is low CREB. In FIG. 4B, in order from right/bottom to left/top, the curves are IR+high CREB, IR+low CREB, CR+high CREB, and CR+low CREB. In FIG. 4C, in order from right/bottom to left/top, the curves are S+high CREB, O+high CREB, S+low CREB, and O+low CREB. In FIG. 4D, the curve to the right and bottom is low APC and the curve to the left and top is high APC. In FIG. 4E, in order from right/bottom to left/top, the curves are IR+high APC, IR+low APC, CR+low APC, and CR+high APC. In FIG. 4F, in order from bottom to top at 4000 days survival, the curves are O+low APC, S+low APC, S+high APC, and O+high APC.

DETAILED DESCRIPTION OF THE INVENTION

Figure 1:
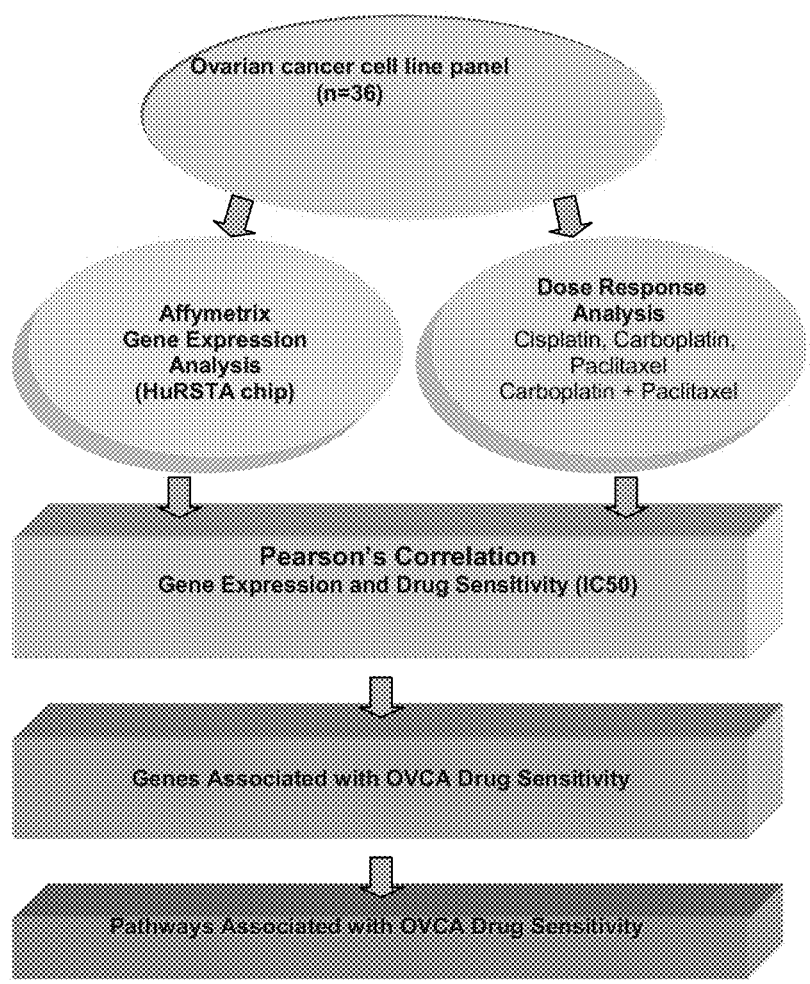
FIG. 1 shows a flow chart of the experimental design and an example of analysis of the correlation of treatments with genes and pathways. Gene expression analysis was performed on a panel of ovarian cancer cell lines (n=36) using the custom Affymetrix HuRSTA chip. Each cell line was treated with increasing doses of carboplatin, cisplatin, paclitaxel, or carboplatin plus paclitaxel, and $IC_{50}$ values were quantified using CellTiter-Blue cell viability assays. Pearson correlation coefficients were calculated for expression data and drug $IC_{50}$ values. Genes associated with OVCA sensitivity (demonstrating expression/$IC_{50}$ correlations, P<0.01) were subjected to GeneGo Metacore Pathway analysis.
Figure 3A:
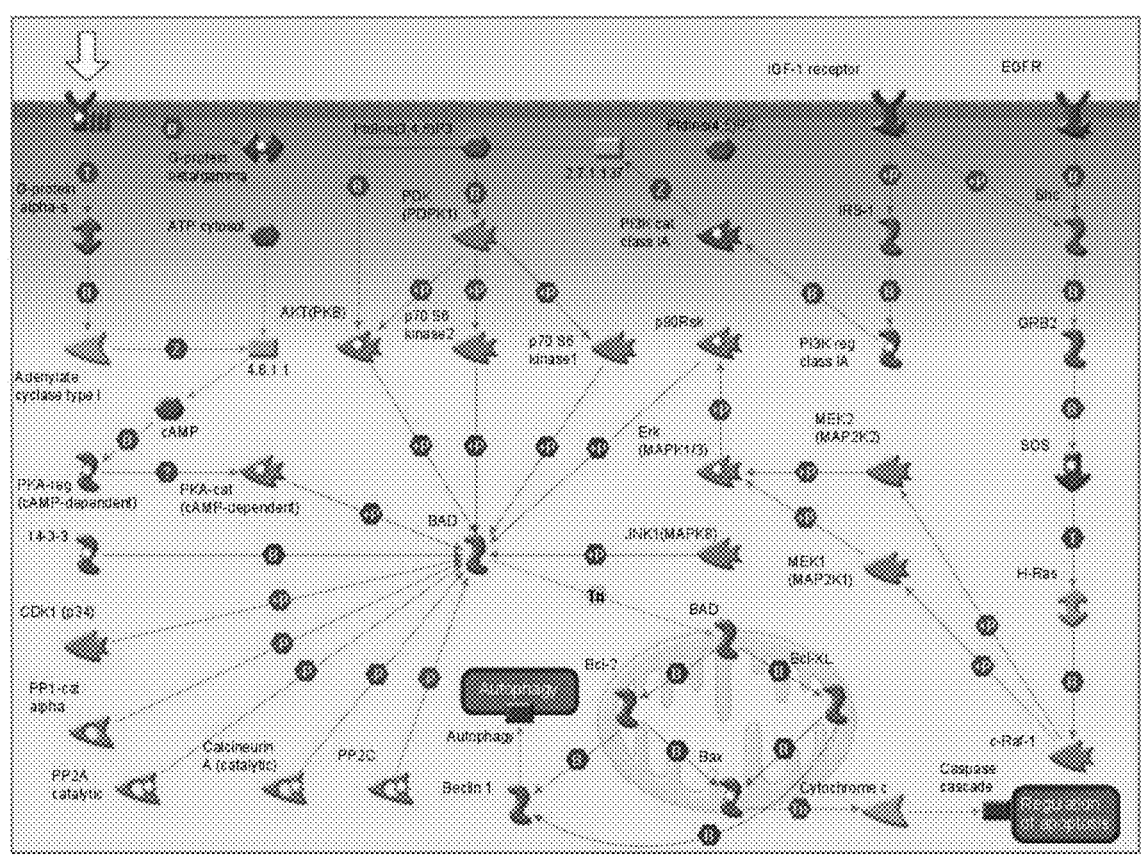
FIGS. 3A-3D are diagrams showing details of the common biological pathways activated in OVCA cells in response to chemotherapeutic agents. Three biological pathways are commonly activated in an OVCA cell line panel in multiple comparisons of chemotherapeutic agent response. A: "Apoptosis and Survival/BAD phosphorylation" pathway. B: "Cell Cycle/Role of APC in Cell Cycle Regulation" pathway. C: "Transcription/CREB" pathway. D: reference list for the annotations used in FIGS. 3A-3C.
Figure 3B:
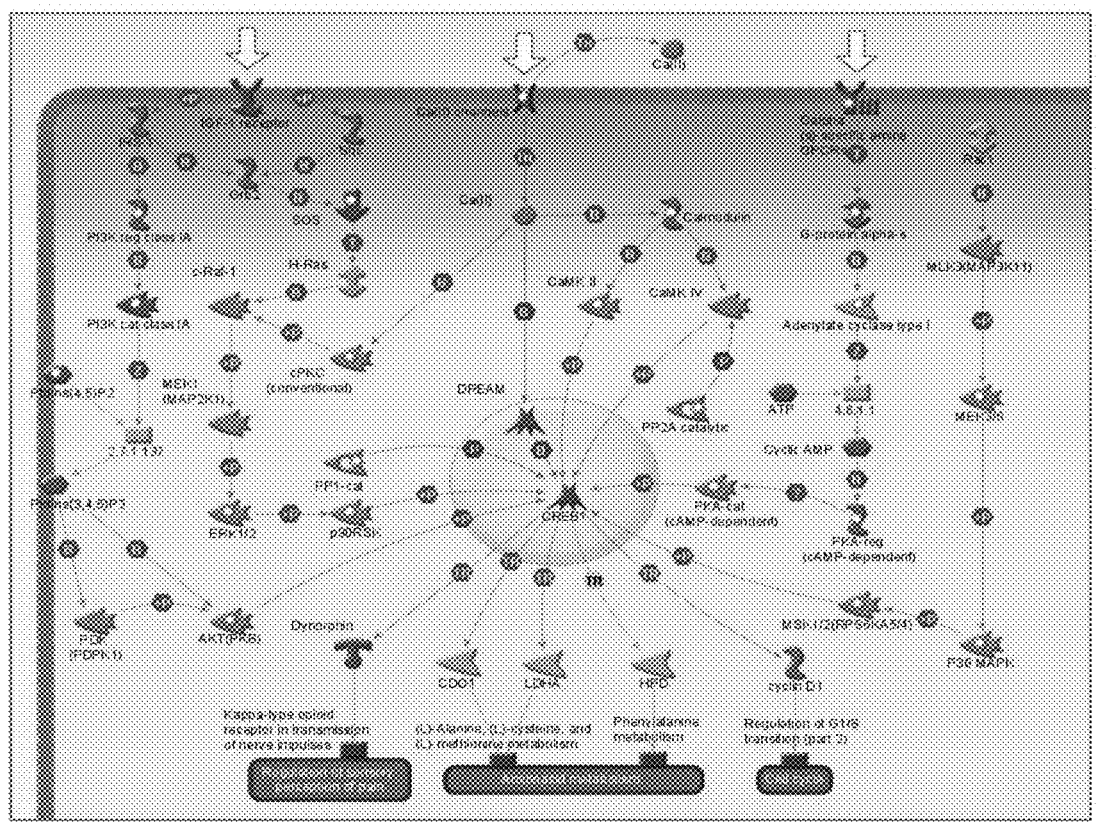
Figure 3C:
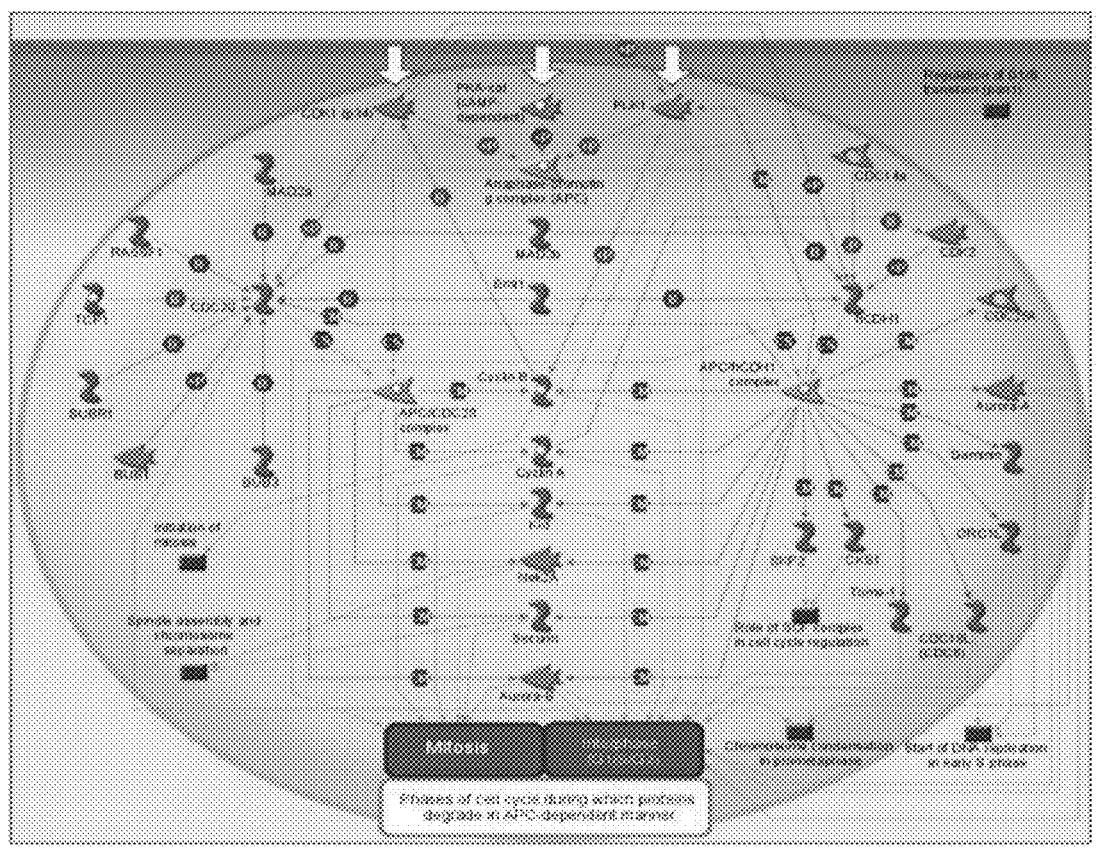
Figure 3D:
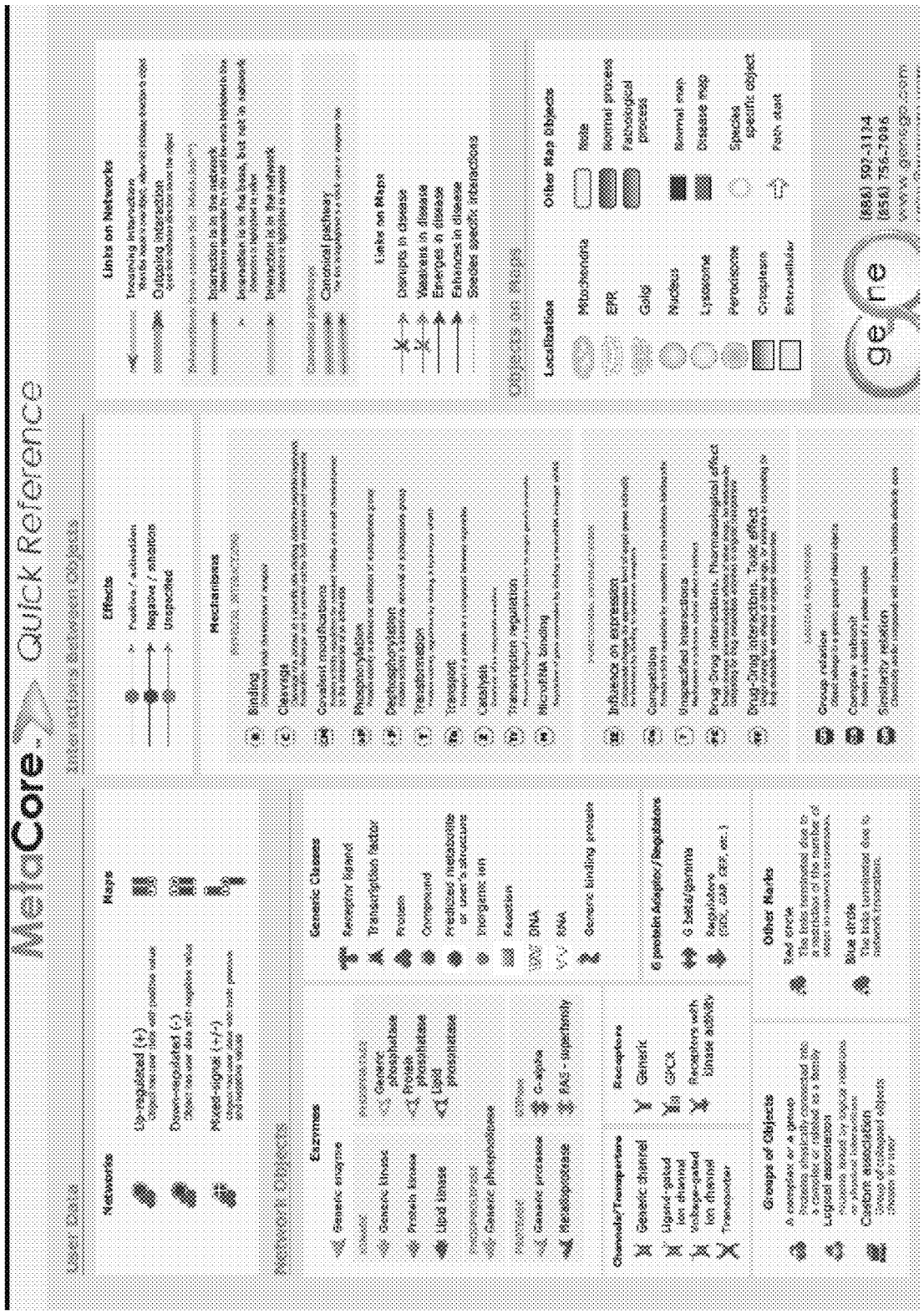

The disclosed method and compositions may be understood more readily by reference to the following detailed description of particular embodiments and the Example included therein and to the Figures and their previous and following description.

Disclosed are compositions and methods for assessing the apoptosis and survival BAD phosphorylation pathway (BAD pathway); and/or (2) the cell cycle role of APC in cell cycle regulation pathway (APC pathway); and/or (3) the transcription CREB pathway (CREB pathway) and for using these pathways to assess, treat, monitor, prognose, diagnose, etc. subjects with cancer. Also disclosed are compositions and methods for identifying molecular pathways that are common to one or more chemotherapeutic agents for the treatment of an oncological disorder, for screening for compounds or agents that can be used to treat ovarian cancer or colon cancer, and for selecting for compounds or agents that can enhance the cytotoxic response of cisplatin, carboplatin, and/or paclitaxel against a cancer cell, such as an ovarian cancer cell or cell line or a colon cancer cell or cell line. In some forms, the disclosed methods can comprise identifying compounds and/or agents that modulate the BAD pathway and/or the APC pathway; and/or the CREB pathway. In some forms, the disclosed methods can comprise method for treating cancer using compounds and/or agents that modulate the BAD pathway and/or the APC pathway; and/or the CREB pathway. Also disclosed are compositions, compounds, and agents identified using the disclosed methods.

It has been discovered that certain signaling pathways are associated with treatment and outcomes for cancers. As described herein, these associations can be used to assess and predict clinical outcomes for cancers and subject with cancer. These associations can also be used to identify cancers and subjects exhibiting or at risk for chemoresistance. Such identified cancers and subjects can be treated with agents that target the associated pathways so as to increase the effectiveness of chemotherapeutic agents. The three common pathways are:

1. Apoptosis and survival_BAD phosphorylation: BAD induces apoptosis by inhibiting anti-apoptotic BCL-2-family members (BCL-x, Bcl-2), allowing other pro-apoptotic proteins (BAK and BAX) to induce release of cytochrome c, followed by caspase activation and apoptosis.

2. Cell cycle Role of APC in cell cycle regulation: Anaphase-promoting complex (APC) a ubiquitin ligase, is required to induce progression and exit from mitosis by inducing proteolysis of different cell cycle regulators.

3. Transcription CREB pathway: Stimulus induced transcription factor cyclic AMP (cAMP) responsive element binding protein 1 (CREB1) is critical for a variety of cellular processes, including proliferation, differentiation and adaptive responses.

Disclosed are methods of assessing a subject with cancer. In some forms, the method comprises determining a CREB pathway gene expression signature score for a cancer sample from the subject, wherein a low CREB pathway gene expression signature score indicates that the subject has greater chance of a positive clinical outcome. A high CREB pathway gene expression signature score indicates that the subject has lower chance of a positive clinical outcome (or a greater chance of a negative clinical outcome). In some forms, the method comprises determining an APC pathway gene expression signature score for a cancer sample from the subject, wherein a high APC pathway gene expression signature score indicates that the subject has greater chance of a positive clinical outcome. A low APC pathway gene expression signature score, or a combination indicates that the subject has lower chance of a positive clinical outcome (or a greater chance of a negative clinical outcome). In some forms, the method comprises determining both a CREB pathway gene expression signature score and an APC pathway gene expression signature score for a cancer sample for a cancer sample from the subject, wherein a low CREB pathway gene expression signature score, a high APC pathway gene expression signature score, or a combination indicates that the subject has greater chance of a positive clinical outcome. A high CREB pathway gene expression signature score, a low APC pathway gene expression signature score, or a combination indicates that the subject has lower chance of a positive clinical outcome (or a greater chance of a negative clinical outcome). In some forms, the method can also comprise determining a BAD pathway gene expression signature score for a cancer sample from the subject, wherein a low BAD pathway gene expression signature score indicates that the subject has greater chance of a positive clinical outcome. A high BAD pathway gene expression signature score indicates that the subject has lower chance of a positive clinical outcome (or a greater chance of a negative clinical outcome). In some forms, the method comprises determining a CREB pathway gene expression signature score for a colon cancer sample from the subject, wherein a high CREB pathway gene expression signature score indicates that the subject with colon cancer has greater chance of a positive clinical outcome. A low CREB pathway gene expression signature score indicates that the subject with colon cancer has lower chance of a positive clinical outcome (or a greater chance of a negative clinical outcome).

As used herein, a "gene expression signature" is a pattern of expression of a defined set of genes (or a subset of a defined set of genes) that is correlated with one or more diseases, conditions, states, phenotypes, etc. of a cell, cells, tissue, organ, organism, subject, species, genus, family, class, etc. The genes in such a defined set of genes can be referred to as "signature genes." As used herein, a "pathway gene expression signature" is a pattern of expression of a defined set of genes (or a subset of a defined set of genes) associated with a cell signaling pathway or metabolic pathway that is correlated with one or more diseases, conditions, states, phenotypes, etc. of a cell, cells, tissue, organ, organism, subject, species, genus, family, class, etc. The genes in such a defined set of genes can be referred to as "signature pathway genes." In the context of a pathway gene expression signature, genes are associated with a pathway if they produce expression products that are in the pathway, affect the expression of the pathway, modulate the pathway activity, or a combination. Examples of association of genes to pathways are described in the Examples herein.

As used herein, a "gene expression signature score" is an average, typically a weighted average, of a gene expression signature. That is, an average of a pattern of expression of a defined set of genes (or a subset of a defined set of genes) that is correlated with one or more diseases, conditions, states, phenotypes, etc. of a cell, cells, tissue, organ, organism, subject, species, genus, family, class, etc. As used herein, a "pathway gene expression signature score" is an average, typically a weighted average, of a pathway gene expression signature. That is, an average of a pattern of expression of a defined set of genes (or a subset of a defined set of genes) associated with a cell signaling pathway or metabolic pathway that is correlated with one or more diseases, conditions, states, phenotypes, etc. of a cell, cells, tissue, organ, organism, subject, species, genus, family, class, etc.

A cancer sample is a sample made up of or derived from a cancer or cancer cells.

Also disclosed are methods of determining the clinical outcome or predicting the clinic outcome of cancer treatment. In some forms, the method comprises determining a CREB pathway gene expression signature score for a cancer sample, where the CREB pathway gene expression signature score indicates the clinical outcome of the treatment on the cancer, where a low CREB pathway gene expression signature score compared to a median CREB pathway gene expression signature score indicates that the subject has greater chance of a positive clinical outcome.

In some forms, the method comprises determining a APC pathway gene expression signature score for a cancer sample, where the APC pathway gene expression signature score indicates the clinical outcome of the treatment on the cancer, where a high APC pathway gene expression signature score compared to a median APC pathway gene expression signature score indicates that the subject has greater chance of a positive clinical outcome.

In some forms, the method comprises determining a CREB pathway gene expression signature score for a colon cancer sample, where the CREB pathway gene expression signature score indicates the clinical outcome of the treatment on the colon cancer, where a high CREB pathway gene expression signature score compared to a median CREB pathway gene expression signature score indicates that the subject with colon cancer has greater chance of a positive clinical outcome.

In some forms, the pathway gene expression signature score can be determined by determining the expression of signature pathway genes, and calculating the pathway gene expression signature score from the expression of signature pathway genes. In some forms, the pathway gene expression signature score can be determined by $\Sigma w_i x_i$, where $x_i$ represents gene i expression level and $w_i$ is the corresponding weight (loading coefficient) with $\Sigma w_i^2 = 1$. A CREB pathway gene expression signature score above the median value indicates poor clinical outcome to the treatment, a CREB pathway gene expression signature score below the median indicates positive clinical outcome to the treatment, an APC pathway gene expression signature score below the median value indicates poor clinical outcome to the treatment, an APC pathway gene expression signature score above the median indicates positive clinical outcome to the treatment, a BAD pathway gene expression signature score above the median value indicates poor clinical outcome to the treatment, and a BAD pathway gene expression signature score below the median indicates positive clinical outcome to the treatment. A CREB pathway gene expression signature score in colon cancer below the median value indicates poor clinical outcome to the treatment and a CREB pathway gene expression signature score in colon cancer above the median indicates positive clinical outcome to the treatment.

Examples of median pathway gene expression signature scores are described in the Examples herein. In general, the median of any gene expression signature scores can be determined and calculated using techniques know to those of skill in the art. Median gene expression signatures can be predetermined, determined as part of the disclosed methods, using cells and samples other than those of the cancer, subject, etc., using cells and samples of the cancer, subject, etc., etc.

Although gene expression signatures can be determined by determining the expression of every gene in the set of signature genes (that is, the genes in the defined set of genes for the gene expression signature at issue), this is not required. Gene expression signatures can be determined from a subset of the signature genes. For example, the expression of at least 10%, 20%, 30%, 40%, 50%, 60%, 70%, 75%, 80%, 85%, 90%, 92%, 94%, 95%, 96%, 97%, 98%, 99%, or 100% of the signature genes can be determined.

The clinical outcome can be any assessment, endpoint, or clinical feature of interest and/or that is relevant to gene expression signature, associated therapies, or combinations. For example, as described herein, certain pathways have been shown to be relevant to the effectiveness of certain therapeutic agents and to certain clinical outcomes. In some forms, the clinical outcome can be chemotherapeutic effect, wherein the chemotherapeutic can be, for example, cisplatin, carboplatin, paclitaxel, or a combination. In some forms, the clinical outcome can be survival, such as days, months, or years of survival following diagnosis, treatment, end of treatment, etc. As another example, the clinical outcome can be cancer-free survival.

In some forms, the cancer can be ovarian cancer, colon cancer, cervical cancer, cervical carcinoma, breast cancer, and epithelial cancer, renal cancer, genitourinary cancer, pulmonary cancer, esophageal carcinoma, gastric cancer, head and neck carcinoma, large bowel cancer, hematopoietic cancers, testicular cancer, rectal cancer, prostate cancer, pancreatic cancer, bladder cancer, pancreatic cancer, skin cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, liver cancer, melanoma, squamous cell carcinomas of the mouth, throat, larynx, and lung, lymphoma, B cell lymphoma, T cell lymphoma, mycosis fungoides, Hodgkin's Disease, or myeloid leukemia.

In some forms, the chance of a positive clinical outcome is greater than the indicated chance of a positive clinical outcome if the cancer exhibited a complete response to chemotherapy. In some forms, the chance of a positive clinical outcome is less than the indicated chance of a positive clinical outcome if the cancer exhibited an incomplete response to chemotherapy. In some forms, the chance of a positive clinical outcome is greater than the indicated chance of a positive clinical outcome if debulking is optimal. In some forms, the chance of a positive clinical outcome is less than the indicated chance of a positive clinical outcome if debulking is suboptimal. The chance of a positive (or negative) clinical outcome is preferably assessed relative to the average or median chance of the outcome. The chance of a positive (or negative) clinical outcome can also be assessed relative to the average or median chance of the outcome of a similar cancer or similarly situated subject.

Also disclosed are methods of treating cancer. In some forms, the method comprises determining a CREB pathway gene expression signature score for a cancer sample from the subject, and administering to the subject an antagonist of the CREB pathway if the cancer sample has a low CREB pathway gene expression signature score. In some forms, the method can further comprise determining an APC pathway gene expression signature score for a cancer sample from the subject, and administering to the subject an agonist of the APC pathway if the cancer sample has a high APC pathway gene expression signature score. In some forms, the method comprises determining an APC pathway gene expression signature score for a cancer sample from the subject, and administering to the subject an agonist of the APC pathway if the cancer sample has a high APC pathway gene expression signature score. In some forms, the method can further comprise determining a CREB pathway gene expression signature score for a cancer sample from the subject, and administering to the subject an antagonist of the CREB pathway if the cancer sample has a low CREB pathway gene expression signature score. In some forms, the method comprises determining a CREB pathway gene expression signature score for a colon cancer sample from the subject, and administering to the subject with colon cancer an antagonist of the CREB pathway if the colon cancer sample has a high CREB pathway gene expression signature score. In some forms, the method can comprise administering a composition or agent that decreases CREP pathway expression. In some forms, the method can comprise administering a composition or agent that increases APC pathway expression. In some forms, the method can further comprise administering a cancer chemotherapeutic to the subject.

Also disclosed are methods for identifying molecular pathways that are common to one or more chemotherapeutic agents for the treatment of an oncological disorder. In some forms, the method comprises (a) contacting a cancer cell or cancer cell line with the one or more agents and quantifying a dose response effect ($IC_{50}$) for each agent or combination of agents, and, in parallel, (b) determining gene expression for each cell or cell line and agent or combination of agents, (c) evaluating gene expression and chemotherapeutic dose response data for each agent or combination of agents for correlation, and (d) analyzing genes that demonstrate expression and dose response ($IC_{50}$) correlations to identify significantly represented molecular pathways, thereby identifying pathways common to one or more of the agents and cells.

In some forms, the oncological disorder can be one that is sensitive to treatment by cisplatin, carboplatin, paclitaxel, or a combination. In some forms, the oncological disorder can be ovarian cancer. In some forms, the oncological disorder can be colon cancer.

Also disclosed are methods for screening for compounds or agents that can be used to treat ovarian cancer or colon cancer. In some forms, the method comprises testing, identifying, or both compounds, agents, or both that target the apoptosis and survival BAD phosphorylation pathway, the cell cycle role of APC in cell cycle regulation pathway, the transcription CREB pathway, or a combination. In some forms, the compound or agent modulates the function, activity, amount, expression, or a combination of an expression product associated with the apoptosis and survival BAD phosphorylation pathway, the cell cycle role of APC in cell cycle regulation pathway, the transcription CREB pathway, or a combination.

Also disclosed are methods for selecting for compounds or agents that can enhance the cytotoxic response of cisplatin, carboplatin, paclitaxel, or a combination against a cancer cell. In some forms, the method comprises testing, identifying, or both compounds or agents that modulate the apoptosis and survival BAD phosphorylation pathway, the cell cycle role of APC in cell cycle regulation pathway, the transcription CREB pathway, or a combination. In some forms, the compound or agent modulates the function, activity, amount, expression, or a combination of an expression product associated with the apoptosis and survival BAD phosphorylation pathway, the cell cycle role of APC in cell cycle regulation pathway, the transcription CREB pathway, or a combination.

Disclosed are methods for identifying molecular pathways that are common to one or more chemotherapeutic agents for the treatment of an oncological disorder. In some forms, the methods can comprise contacting a cancer cell or cancer cell line with the one or more agents and quantifying a dose response effect (IC50) for each agent and/or combination of agents and, in parallel, determining gene expression for each cell or cell line and agent and/or combination of agents. Gene expression and chemotherapeutic dose response data can then be evaluated for each agent and/or combination of agents for correlation (e.g., Pearson's correlation). Genes that demonstrate expression and dose response (IC50) correlations can then be analyzed to identify significantly represented molecular pathways wherein pathways common to one or more of the agents and cells can be identified.

Disclosed are methods for screening for compounds or agents that can be used to treat ovarian cancer or colon cancer. In some forms, the methods can comprise testing and identifying compounds and/or agents that target (1) the apoptosis and survival BAD phosphorylation pathway (BAD pathway); and/or (2) the cell cycle role of APC in cell cycle regulation pathway (APC pathway); and/or (3) the transcription CREB pathway (CREB pathway).

Disclosed are methods for selecting for compounds or agents that can enhance the cytotoxic response of cisplatin, carboplatin, and/or paclitaxel against a cancer cell, such as an ovarian cancer cell or cell line or a colon cancer cell or cell line.

Also disclosed are compounds and agents identified using the subject methods.

Compounds and agents that can be screened using the disclosed methods include, but are not limited to, organic and inorganic compounds, lipids, carbohydrates, proteins, and nucleic acids (e.g., siRNA, antisense oligonucleotides, etc.). For example, organic compounds can be screened for those that bind to a molecular component of a pathway associated with cancer, such as the disclosed pathways. As a specific example, an organic compound can be screened for inhibition or blocking of the 90 kDa ribosomal S6 kinase (p90RSK) phosphorylation of BAD. Similarly, compounds can be screened for those that modulate expression of a gene or molecular component of a common pathway to the cancer, treatment, etc. being assessed, such as the disclosed pathways. For example, the compound can be an siRNA that targets expression of a gene whose gene product is a molecular component of a pathway associated with cancer, such as the disclosed pathways.

In-vitro chemosensitivity and genome-wide expression data has been integrated to define molecular pathways associated with ovarian cancer chemosensitivity. These pathways are also associated with overall patient survival. OVCA cell line chemosensitivity data has been integrated with measures of genome-wide expression to provide insights into the biologic basis to OVCA response to agents used in primary therapy. The findings identify pathways that can be common determinants of response to single agent platinum, and also platinum/taxane combination therapies, and which may aid rational selection of targeted agents that enhance cytotoxic response in future.

Carboplatin and cisplatin, alone or in combination with paclitaxel, have been shown to have similar efficacies against ovarian cancer (OVCA) yet exhibit different toxicity profiles. The molecular basis of OVCA response to these drugs, in combination or as single agents, remains to be fully delineated. The objective was to characterize the common and unique cellular pathways that underlie OVCA response and analyze whether these play a role in OVCA survival. OVCA cell lines (n=36) were treated with carboplatin, cisplatin, paclitaxel, or carboplatin-paclitaxel (CPTX), and $IC_{50}$ levels were quantified using CellTiter-Blue assays. In parallel, pre-treatment gene expression analyses were performed on each cell line. Pearson correlation coefficients were calculated for expression data and $IC_{50}$. Genes demonstrating expression/$IC_{50}$ correlations (P<0.01) were subjected to biological pathway analysis. An independent OVCA clinico-genomic dataset (n=142) was evaluated for clinical features associated with represented pathways. Cell line sensitivity to carboplatin, cisplatin, paclitaxel, and CPTX was associated with the expression of 77, 68, 64, and 25 biological pathways (P<0.01), respectively. Three pathways ("Apoptosis and Survival/BAD Phosphorylation," "Role of APC in Cell Cycle Regulation," and "Transcription/CREB") were common between carboplatin-cisplatin, cisplatin-CPTX, and carboplatin-CPTX comparisons. Transcription/CREB pathway expression was associated with OVCA overall survival. Integration of OVCA cell line chemo-sensitivity and genome-wide expression data identified the Transcription/CREB pathway to be associated with OVCA cell line platinum sensitivity and OVCA overall survival. Such information may aid patient stratification and future efforts aimed at rational selection of targeted agents that enhance OVCA cytotoxic response to platinum-based therapy.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a gene expression signature is disclosed and discussed and a number of modifications that can be made to a number of gene expression signatures including the gene expression signature are discussed, each and every combination and permutation of the gene expression signature and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

As used herein, the term "activity" refers to a biological activity.

As used herein, the term "pharmacological activity" refers to the inherent physical properties of a peptide or polypeptide. These properties include but are not limited to half-life, solubility, and stability and other pharmacokinetic properties.

A. Compounds

The disclosed methods include gene expression signatures that are associated with certain therapies, including, for example, therapeutic agents such as anti-cancer agents. The disclosed methods also make use of such anti-cancer agents to treat cancers assessed according to the disclosed methods. Although the disclosed methods preferably involve the use of therapeutic agents associated with the gene expression signatures used to assess the disease and the use of therapeutic agents that can affect pathways associated with the pathway gene expression signatures used, other therapeutic agents can also be used. In some forms, the therapeutic agent can be a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a platinum agent such as cisplatin, carboplatin, or oxaliplatin; a taxane such as docetaxel; an anthracyclin such as doxorubicin; an alkylating agent; a vinca alkaloid; an anti-metabolite such as methotrexate; a steroid; an antibiotic such as adriamycin; a ifosfamide; or a selective estrogen receptor modulator; an antibody such as trastuzumab; paclitaxel such as Abraxane.

Platinum agents are useful cancer chemotherapeutic agents. Such a platinum agent can be, for example, cisplatin, carboplatin, or oxaliplatin as described, for example, in Crown, Seminars in Oncol. 28:28-37 (2001). Other useful cancer chemotherapeutic agents include, without limitation, mitomycin-C, adriamycin (doxorubicin), and ansamycins.

Taxanes are chemotherapeutic agents useful with the compositions disclosed herein. Useful taxanes include, without limitation, docetaxel (Taxotere; sanofi-aventis; Parsippany, N.J.) and paclitaxel (Taxol; Bristol-Myers Squibb; Princeton, N.J.). See, for example, Chan et al., J. Clin. Oncol. 17:2341-2354 (1999), and Paridaens et al., J. Clin. Oncol. 18:724 (2000).

An alkylating agent such as melphalan, ifosfamide, or chlorambucil also can be a useful cancer chemotherapeutic agent. Similarly, a vinca alkaloid such as vindesine, vinblastine or vinorelbine; or an antimetabolite such as 5-fluorouracil, 5-fluorouridine, methotrexate, or a derivative thereof can be a useful cancer chemotherapeutic agent.

A cancer chemotherapeutic agent useful for treatment of breast cancer and other hormonally-dependent cancers also can be an agent that antagonizes the effect of estrogen, such as a selective estrogen receptor modulator or an anti-estrogen. The selective estrogen receptor modulator, tamoxifen, is a cancer chemotherapeutic agent that can be used in a composition for treatment of breast cancer (Fisher et al., J. Natl. Cancer Instit. 90:1371-1388 (1998)).

The therapeutic agent can be an antibody such as a humanized monoclonal antibody. As an example, the anti-epidermal growth factor receptor 2 (HER2) antibody, trastuzumab (Herceptin; Genentech, South San Francisco, Calif.) can be a therapeutic agent useful for treating HER2/neu overexpressing breast cancers (White et al., Annu Rev. Med. 52:125-141 (2001)).

Useful therapeutic agents also can be a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *Ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed compositions and methods.

In some forms, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon-α (IFN-α); interferon-γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art. It is understood that these and other polypeptides with biological activity can be a "therapeutic polypeptide."

A therapeutic agent can also be an anti-angiogenic agent. As used herein, the term "anti-angiogenic agent" means a molecule that reduces or prevents angiogenesis, which is the growth and development of blood vessels. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Some other examples of useful therapeutic agents include nitrogen mustards, nitrosoureas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Chlomaphazine, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel (TAXOTERE®, Rhone-Poulenc Rorer, Antony, France), Doxil, Doxorubicin, DTIC, Epirubicin, Estramustine, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, mechlorethamine oxide hydrochloride, Melphalan, Mercaptopurine, Methotrexate, Mitomycin, Mitotane, Mitoxantrone, Novembiehin, Oxaliplatin, Paclitaxel (TAXOL®, Bristol-Myers Squibb Oncology, Princeton, N.J.), Pamidronate, Pentostatin, Phenesterine, Plicamycin, Prednimustine, Procarbazine, Rituximab, Steroids, STI-571, Streptozocin, Tamoxifen, Temozolomide, Teniposide, Tetrazine, Thioguanine, Thiotepa, Tomudex, Topotecan, Treosulphan, Trimetrexate, Trofosfamide, Vinblastine, Vincristine, Vindesine, Vinorelbine, VP-16, and Xeloda. Alkylating agents such as Thiotepa and; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, triethylenephosphoramide, triethylenethiophosphaoramide and trimethylolomelamine; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK; Razoxane; Sizofrran; Spirogermanium; tenuazonic acid; triaziquone; 2,2',2''-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotepa; taxoids, e.g., Paclitaxel and Doxetaxel; Gemcitabine; 6-thioguanine; Mercaptopurine; Methotrexate; platinum analogs such as Cisplatin, Carboplatin, and Oxaliplatin; etoposide (VP-16); Ifosfamide; Mitomycin C; Mitoxantrone; Vinblastine; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above. Useful therapeutic agents include, for example, doxorubicin, Herceptin, and liposomal doxorubicin.

It is understood by one skilled in the art of medicinal oncology that these and other agents are useful therapeutic agents, which can be used separately or together in the disclosed compositions and methods. Thus, it is understood that the compositions disclosed herein can contain one or more of such therapeutic agents and that additional components can be included as part of the composition, if desired. As a non-limiting example, it can be desirable in some cases to utilize an oligopeptide spacer between the disclosed peptides, amino acid sequences, and annexin 1-binding compounds and the therapeutic agent (Fitzpatrick and Garnett, Anticancer Drug Des. 10:1-9 (1995)).

The effectiveness of a therapeutic agent can be enhanced by modulating pathway(s) with which the therapeutic agent. For example, appropriate modulation of the CREB pathway, the APC pathway, and/or the BAD pathway can be used to enhance the effectiveness of platinum-based agents. The appropriate modulation of a given pathway generally will be to counter the expression, activity, or effect of the pathway that is associated with poor clinical outcomes, especially resistance to the agent. For example, an agonist of the APC pathway and/or a composition or agent that increases APC pathway expression can be used if the cancer sample has a high APC pathway gene expression signature score. As another example, an antagonist of the CREB pathway and/or a composition or agent that decreases CREP pathway expression if the cancer sample has a low CREB pathway gene expression signature score. As another example, an antagonist of the BAD pathway and/or a composition or agent that decreases BAD pathway expression if the cancer sample has a low BAD pathway gene expression signature score. As another example, an agonist of the CREB pathway and/or a composition or agent that increases CREP pathway expression if the colon cancer sample has a low CREB pathway gene expression signature score.

Pathways often have many components, multiple effects, and multiple points of regulation (see FIG. 3). Thus, modulation of a pathway can be effected through multiple components, activities, and effects. Generally, the aspect of a pathway's activities and effects that are associated with chemoresistance and other cancer promoting effects are preferred for targeting and can be used to define appropriate modulation of the pathway for a given cancer and therapy. FIG. 3 shows details of the CREB pathway, the APC pathway, and the BAD pathway. Such information can be used by those of skill in the art to choose pathway activities and effects for appropriate modulation. Without wishing to be limited to a particular mechanism of action, the discussion below provides examples of how pathway activities and effects can be seen to affect chemosensitivity and chemoresistance, and to promote cancer.

CREB (cAMP response element binding protein) is a transcription factor that can be activated by multiple pathways that affect cellular cAMP levels, and its many targets play important roles in cellular metabolism, proliferation, and survival (Mayr & Montminy, 2001; Zhang et al, 2005). G-protein-coupled receptors, transmembrane proteins that transduce extracellular signals to intracellular effector pathways via heterotrimeric G proteins, activate the enzyme adenylate cyclase, which catalyzes the conversion of ATP to cAMP. cAMP then binds the regulatory subunits of protein kinase A (PKA), which leads to the release of the PKA catalytic subunits (Lappano & Maggiolini). Active PKA migrates to the nucleus, where it phosphorylates CREB (Gonzalez & Montminy, 1989). Phosphorylated CREB then binds its coactivator CBP/p300, a histone acetyltransferase, and together CREB and CBP/p300 activate the transcription of genes whose promoters contain a CRE (cAMP response element) sequence (Bannister & Kouzarides, 1996; Parker et al, 1996). CREB overexpression may be required for the proliferation and survival of human cancers (Bonni et al, 1999; Siu & Jin, 2007). Additionally, the CREB coactivator CBP/p300 is mutated in several human cancers, with loss of CBP/p300 histone acetyltransferase activity potentially impacting the expression of several tumor suppressor targets (Iyer et al, 2004).

The anaphase-promoting complex/cyclosome (APC/C) is a multi-subunit ubiquitin ligase required for regulation of cell cycle progression and mitotic exit. APC/C consists of multiple core subunits and an activator component. APC/C is tightly regulated during the cell cycle via the cyclical binding of the Cdc20 (cell division cycle 20) and Cdh1 (cell division cycle homolog 1) activating subunits. The major role of APC/C is to target substrates for proteasomal degradation in an orchestrated manner, with Cdc20 and Cdh1 mediating substrate recognition to ensure that mitotic entry and exit occur correctly. APC/C$^{Cdc20}$ is active from anaphase to the end of mitosis, and APC/C$^{Cdh1}$ is active from late mitosis to the $G_1$-S transition. APC/C$^{Cdc20}$-mediated destruction of targets such as securin and cyclin B drives chromosome separation and exit from mitosis. As mitotic cyclins are degraded, cyclin-dependent kinase activity decreases. By late M phase, Cdh1 is no longer phosphorylated and can bind to the core APC/C subunits. APC/C$^{Cdh1}$ has multiple targets, including Cdc20, mitotic cyclins, mitotic kinases, and inhibitors of DNA replication origin licensing. Collectively, degradation of APC/C$^{Cdh1}$ targets ensures that cells do not duplicate their DNA and/or enter mitosis prematurely (Nakayama & Nakayama, 2006). Because of the critical role of APC/C in regulating chromosome segregation during mitosis, deregulation of the complex could cause genomic instability and contribute to tumorigenesis. Indeed, loss of function mutations of core APC/C subunits has been observed in colorectal cancer cells, upregulation of Cdc20 has been observed in several human cancers, and loss of Cdh1 causes chromosomal instability and tumor formation in mice (Garcia-Higuera et al, 2008; Nakayama & Nakayama, 2006; Wang et al, 2003).

BAD (BCL-xL/BCL-2-associated death promoter) was first identified in a yeast two-hybrid screen for BCL-2 interactors (Yang et al, 1995). Heterodimerization between BAD and BCL-2, BCL-xL, or BCL-W promotes apoptosis through the displacement of BAK and BAX (Holmgreen et al, 1999; Yang et al, 1995). The interaction between BAD and its partners is dependent on the BAD BH3 domain (Zha et al, 1997). Upon apoptotic stimuli, BAD translocates from the cytosol to the mitochondria (Jia et al, 1999; Zha et al, 1996) where it neutralizes the anti-apoptotic proteins and promotes mitochondrial membrane permeabilization (Datta et al, 2000; Roy et al, 2009). Subversion of BAD-mediated apoptosis may thus be an important mechanism by which tumor cells acquire resistance to apoptotic stimuli. A role of BAD-induced apoptosis in tumor suppression is supported by the identification of BAD mutations in colon cancer that disrupt binding to BCL-2 and BCL-xL and the observation that BAD-deficient mice are prone to diffuse B cell lymphoma (Lee et al, 2004; Ranger et al, 2003). Furthermore, because post-translational modification of BAD represents a key control point between cell survival and apoptosis, BAD phosphorylation is frequently deregulated in cancer. Activation of multiple signaling pathways by growth factors, cytokines, or oncogenic mutations can contribute to increased BAD phosphorylation, with aberrant kinase and phosphatase activity leading to BAD inactivation and resistance to cell death signaling in tumors (Danial, 2008).

BAD, CREB, and APC/C may be linked by common signaling molecules, as signaling pathways converge in many ways to regulate cellular proliferation and survival at both the transcriptional and post-transcriptional levels. For example, PKA phosphorylation activates CREB and inactivates BAD and APC/C$^{Cdc20}$ (Gonzalez & Montminy, 1989; Harada et al, 2001; Lizcano et al, 2000; Searle et al, 2004). AKT also phosphorylates BAD and CREB, and AKT phosphorylation protects some APC/C$^{Cdh1}$ substrates from degradation (Datta et al, 1997; del Peso et al, 1997; Gao et al, 2009). PTEN can also promote the association between APC/C and Cdh1 to prevent S phase entry (Song et al). Cyclin-dependent kinases phosphorylate BAD, APC/C, and CBP/p300 (Ait-Si-Ali et al, 1998; Konishi et al, 2002; Zachariae et al, 1998). There may also be more direct crosstalk between BAD, CREB, and APC. BAD has been linked to regulation of cell cycle progression and has been found at CREs in cyclin genes (Chattopadhyay et al, 2001; Fernando et al, 2007). The APC/C subunits APC5 and APC7 directly bind CBP/p300, stimulate CBP/p300 histone acetyltransferase activity, and potentiate CBP/p300-dependent transcription (Turnell et al, 2005). CREB may also directly impact cell survival by binding to CREs in the promoters of anti-apoptotic factor genes such as BCL-2 to induce their transcription (Wilson et al, 1996).

Based on the known interactions between these proteins, BAD, APC/C, and CREB may interact in a common pathway to induce cell cycle arrest and death in response to mitotic or metabolic stress caused by carboplatin, cisplatin, and paclitaxel. Deregulation of components of these pathways may thus lead to acquired drug resistance. Indeed, abnormal cell cycle progression, defective apoptosis, and metabolic reprogramming have been implicated as key mechanisms of OVCA chemoresistance (Etemadmoghadam et al, 2009; Hajra et al, 2008; Montopoli et al; Takahashi et al, 2005).

B. Administration

The disclosed methods can involve administration of composition, compounds, agents, etc. to cells, tissues, organs, subjects, etc. Any suitable techniques, systems, adjutants, deliver systems, etc. can be used.

The term "hit" refers to a test compound that shows desired properties in an assay. The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist."

The term "inhibit" means to reduce or decrease in activity or expression. This can be a complete inhibition or activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, ameliorization, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

In one aspect, the compounds described herein can be administered to a subject comprising a human or an animal including, but not limited to, a mouse, dog, cat, horse, bovine or ovine and the like, that is in need of alleviation or amelioration from a recognized medical condition.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need of treatment of cancer or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

By "pharmaceutically acceptable" is meant a material that is not biologically or otherwise undesirable, i.e., the material can be administered to an individual along with the selected compound without causing any undesirable biological effects or interacting in a deleterious manner with any of the other components of the pharmaceutical composition in which it is contained.

Any of the compounds having the formula I can be used therapeutically in combination with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The compounds and pharmaceutical compositions described herein can be administered to the subject in a number of ways depending on whether local or systemic treatment is desired, and on the area to be treated. Thus, for example, a compound or pharmaceutical composition described herein can be administered as an ophthalmic solution and/or ointment to the surface of the eye. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

C. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for assessing cancers and subject, the kit comprising reagents for determining gene expression levels and signatures. The kits also can contain enzymes, labels, and buffers.

D. Mixtures

Disclosed are mixtures formed by performing or preparing to perform the disclosed method. For example, disclosed are mixtures comprising a platinum agent and a cancer sample.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

E. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising a device for determining gene expression levels, reagents for determining gene expression levels, and a medium for storing and/or displaying gene expression levels.

F. Data Structures and Computer Control

Disclosed are data structures used in, generated by, or generated from, the disclosed method. Data structures generally are any form of data, information, and/or objects collected, organized, stored, and/or embodied in a composition or medium. A gene expression signature stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

G. Uses

The disclosed methods and compositions are applicable to numerous areas including, but not limited to, assessment of cancers and subject with cancer, and treatment of cancers and subjects with cancer. Other uses include identification of pathways associated with the effectiveness or lack or effectiveness, or both of particular cancer therapies. Other uses are disclosed, apparent from the disclosure, and/or will be understood by those in the art.

EXAMPLES

H. Example 1

Identification and Analysis of Correlations of Genes and Pathways with Cancer Treatments and Outcomes In this example, the objective was to characterize the common and unique cellular pathways that underlie OVCA response and to analyze whether these pathways play a role in OVCA survival. Chemo-sensitivity data from OVCA cell lines treated with single-agent platinum and platinum-taxane combination therapy were integrated with genome-wide expression data to provide insights into the biological basis of OVCA response to primary therapy agents. The identification of unique and shared determinants of drug response in OVCA can be used to improve both the stratification of patients for treatment with therapies and the rational selection of agents targeted to these pathways for treatment of OVCA. The disclosed methods represent examples of such uses.

1. Materials and Methods i. Cell Culture

Ovarian cancer cell lines were obtained from the American Type Culture Collection (Manassas, Va.) (CAOV3, OV90, OVCAR3, SKOV3, TOV112D); from the European Collection of Cell Cultures, Salisbury, UK (A2780CP, A2780S); or from Kyoto University, Kyoto, Japan (CHI, CHIcisR, M41, M41CSR, Tyknu, and TyknuC is R) or were kind gifts from Dr. Patricia Kruk, Department of Pathology, College of Medicine, University of South Florida, Tampa, Fla., and Susan Murphy, PhD, Dept of OBGYN/Division of GYN Oncology, Duke University, Durham, N.C. (A2008, C13, CAOV2, FUOV1, HeyA8, IGR-OV1, IMCC3, IMCC5, MCAS, OV2008, OVCA420, OVCA429, OVCA432, OVCA433, OVCAR4, OVCAR5, OVCAR8, Dov13, BG1, Ovary1847, OVCAR10, OVCAR2, SK-OV-4).

Cell lines were maintained in RPMI-1640 (Invitrogen, Carlsbad, Calif.) supplemented with 10% fetal bovine serum (Fisher Scientific, Pittsburgh, Pa.), 1% sodium pyruvate, 1% penicillin/streptomycin (Cellgro, Manassas, Va.), and 1% nonessential amino acids (HyClone, Hudson, N.H.). Mycoplasma testing was performed every 6 months following manufacturer's protocol (Lonza, Rockland, Me.).

ii. RNA Extraction and Microarray Expression Analysis

RNA from 36 OVCA cell lines was extracted using RNeasy kit following manufacturer's recommendations (Qiagen, Valencia, Calif.). Quality of the RNA was measured using an Agilent 2100 Bioanalyzer. The targets for Affymetrix DNA microarray analysis were prepared according to the manufacturer's instructions, and targets were hybridized to customized Human Affymetrix HuRSTA gene chips (HuRSTA-2a520709), which include 60,607 probe sets and representation of 19,308 genes (Gene Expression Omnibus accession number GSE34615).

iii. CellTiter-Blue Cell Viability Assays

Drug activity was evaluated using a high-throughput CellTiter-Blue cell viability assay. Cells ($2.5 \times 10^3$/well) were plated in 384-well plates using complete media with 10% fetal bovine serum and allowed to adhere overnight. After cell adherence, increasing concentrations of cisplatin, carboplatin (Sigma-Aldrich, St. Louis, Mo.), paclitaxel (Sequoia Research Products Ltd., Pangbourne, UK), or carboplatin plus paclitaxel (carbotaxol: constant molar ratio of carboplatin to paclitaxel of 20,000:1) were added to appropriate wells using an automated pipetting station. Four replicate wells were used for each drug concentration and vehicle controls. Drug dilutions initially consisted of 1.5-fold serial dilutions from a maximum concentration of 100 µM. The cells were incubated with the drug for 72 hours, and 5 µL of CellTiter-Blue reagent (Promega Corp) was added to each well. Fluorescence was read at 579 nm excitation/584 nm emission using a Synergy 4 microplate reader (Bio-Tek Instruments, Inc., Winooski, Vt.). $IC_{50}$ results were determined using a sigmoidal equilibrium model fit (XLfit 5.2, ID Business Solutions Ltd.). $IC_{50}$ was defined as the concentration of drug required for a 50% reduction in growth/viability.

iv. Statistical Analysis

Expression data from 36 OVCA cell lines were subjected to background correction and normalization using the Robust Multichip Average algorithm in the Affymetrix Expression Console (web site affymetrix.com/products/software/specific/expression_console_software.affx). Pearson correlation test was performed on individual gene expression values and $IC_{50}$ results. Probe sets with $P<0.01$ were considered to have significant correlations with $IC_{50}$ results and were uploaded to GeneGo MetaCore for pathway analysis (web site genego.com/metacore.php). Pathways with $P<0.05$ were considered significant, based on the GeneGo MetaCore™ statistical test for significance.

v. Primary OVCA Patient Samples

Genome-wide expression data was evaluated from 142 patients treated at Duke and Moffitt Cancer Centers (including 114, previously reported, Dressman et al. 2007 (Dressman et al, 2007), and 28 new samples). Patients treated at Duke and Moffitt Cancer Centers for whom genomic data were analyzed in the current study had a mean age of 56 years and included 101 patients who demonstrated a CR to primary therapy and 41 who demonstrated an IR. Cytoreductive surgery was optimal for 73 patients and suboptimal for 68. The number of patients with grade 1 disease was 6, grade 2 was 61, grade 3 was 73, with grade unknown for two patients. Race data for this group included: Caucasian, 117; African-American, 18; Asian, 4; Hispanic, 1; and unknown, 2.

Inclusion criteria for all 142 patients (including those treated at Moffitt, Duke) included: (a) a pathologically confirmed diagnosis of serous epithelial ovarian cancer, (b) age>18 years, (c) surgically confirmed advanced stage (III/IV) disease, (d) primary surgical cytoreductive surgery prior to chemotherapy, (e) primary chemotherapy with a platinum-based regimen (+/−taxane or cyclophosphamide).

Exclusion criteria for all 142 patients (including those treated at Moffitt, Duke) included: (a) non-epithelial cancer, (b) borderline tumors, (c) non-serous tumors, (d) early stage (I/II) disease, (e) absence of pathologic documentation of diagnosis, (f) recurrent disease, (g) receipt of neoadjuvant chemotherapy, (h) unknown clinical response to primary therapy.

vi. Building Signatures of Pathway Activity

The principal component analysis (PCA) methodology was used to derive a pathway gene expression signature with a corresponding "pathway score" to represent an overall gene expression level for the pathways of interest. First, data were reduced into a small set of uncorrelated principal components. This set of principal components was generated based on its ability to account for variation. The first PCA is used to represent the overall expression level for the pathway as it accounts for the largest variability in the data. That is, pathway score is equal to $\Sigma w_i x_i$, a weighted average expression among the pathway genes, where $x_i$ represents gene i expression level, $w_i$ is the corresponding weight (loading coefficient) with $\Sigma w_i^2 = 1$, and the $w_i$ values maximize the variance of $\Sigma w_i x_i$.

vii. Validation of Signatures in Primary OVCA Datasets

The pathway gene expression signature scores developed in OVCA cell lines were evaluated in an independent clinico-genomic dataset from 142 OVCA samples treated at Duke and Moffitt Cancer Centers (including 114 previously reported (Dressman et al, 2007) and 28 new samples). In brief, all 142 patients signed the IRB-approved, written informed consent forms, were known to have advanced-stage (III/IV) serous epithelial OVCA, and underwent primary cytoreductive surgery followed by primary therapy with a platinum-based regimen (with or without taxane or cyclophosphamide).

Using genomic data from the panel of 36 OVCA cells, principal component analysis was used to derive: (i) an APC/cell cycle regulation pathway, and (ii) a CREB transcription control pathway gene expression signature. A BAD/Apoptosis and survival pathway signature and its associations with chemo-sensitivity and overall survival was analyzed earlier (Marchion 2011). For both pathways, principal components analysis (PCA) methodology was used to derive a pathway gene expression signature with a corresponding "pathway score" to represent an overall gene expression level for the pathway genes. The generation of the signature used data from cell lines only; no patient data were used. That is, no data from the Duke/MCC samples were used in the initial development/generation of the APC/cell cycle regulation pathway, or CREB transcription control pathway signature; the Duke/MCC ovarian data was a completely independent evaluation set. Specifically, using genomic and $IC_{50}$ data from 36 OVCA cell lines, Pearson correlation was used to identify genes associated with sensitivity ($IC_{50}$) to cisplatin, carboplatin, paclitaxel, and carboplatin with paclitaxel combination (20,000:1 ratio). Expression was calculated using the robust multi-array average algorithm (Irizarry et al, 2003) implemented in Bioconductor (web site bioconductor.org) extensions to the R-statistical programming environment as described previously (Bolstad et al, 2003). Probe sets with expression ranges <2-fold (maximum/minimum) and control probes (i.e., AFFX_*probe sets) were excluded from the analysis. For each cell line, Pearson correlation coefficients were calculated for expression data and drug $IC_{50}$. Genes/probe sets demonstrating expression/$IC_{50}$ correlations ($|R|>0.85$) were subjected to biological pathway analysis using GeneGo/MetaCore™ software, and maps/pathways were identified using the GeneGo/MetaCore™ statistical test for significance (P<0.001). In this way, (i) the BAD apoptosis pathway, (ii) APC/cell cycle regulation pathway, and (iii) CREB transcription control pathway were found to be associated (P<0.05) with cell line drug sensitivity. Data for the BAD pathway has been evaluated and is described in Marchion 2011 and in PCT Application No. PCT/US2012/026617, both of which are hereby incorporated by reference in their entirety and specifically for the correlations identified.

To build pathway-specific PCA scores for APC/cell cycle regulation, and CREB transcription control pathways, initially GeneGo/MetaCore™-defined objects (genes) within each of the pathways (associated with OVCA cell line $IC_{50}$) were identified. Next, for both pathways, and for each pathway object identified in this way, all probesets were selected and used for generation of the PCA score. For the APC/cell cycle regulation pathway, these 119 probesets represented 55 genes. For the CREB transcription control pathway these 287 probesets represented 103 genes. Using all 119 and 287 probesets, respectively, principal component analysis was performed to reduce data dimension into a small set of uncorrelated principal components for both pathways. These sets of principal components were generated based on their ability to account for variation. The first principal component (1st PCA) was used, as it accounts for the largest variability in the data, as a pathway score to represent the overall expression level for each pathway. That is, pathway score=$\Sigma w_i x_i$, a weighted average expression among the APC/cell cycle regulation and CREB transcription control pathway genes (independently for each pathway), where $x_i$ represents gene i expression level, $w_i$ is the corresponding weight (loading coefficient) with $\Sigma w_i^2 = 1$, and the $w_i$ values maximize the variance of $\Sigma w_i x_i$. This approach has been used to derive a malignancy pathway gene signature in a breast cancer study (Chen et al). The APC/cell cycle regulation pathway and CREB transcription control pathway gene expression signature scores developed in OVCA cell lines were evaluated in an independent set of 142 OVCA samples from MCC and Duke University Medical Center (OVCA 142 dataset). For the clinical-genomic OVCA dataset, log-rank test with Kaplan-Meier survival curves was used to test any association between the pathway score ("high versus "low" based upon a median value cut-off) and overall survival for patients with OVCA. No data from the Duke/MCC samples was used to identify the APC/cell cycle regulation pathway, and CREB transcription control pathway gene expression signature; the Duke/MCC ovarian dataset was a completely independent evaluation set.

viii. Defining Clinical Response

Using medical record review, overall survival was evaluated and all 289 OVCA samples were characterized as CR or incomplete responder (IR) to primary platinum-based therapy using criteria described previously (Dressman et al, 2007). Clinical response to primary therapy (surgery plus platinum-based chemotherapy) was therefore established for all 289 patients using standard WHO criteria for patients with measurable disease (Miller et al, 1981). CA-125 was used to classify responses only in the absence of a measurable lesion (e.g. patients subject to optimal cytoreductive surgery); CA-125 response criteria were based on established guidelines (Rustin et al, 1999; Rustin et al, 1996). A complete-response (CR) was defined as a complete disappearance of all measurable and assessable disease or, in the absence of measurable lesions, a normalization of the CA-125 level after adjuvant therapy. Patients were considered to have an incomplete-response (IR) if they demonstrated only a partial response, had stable disease, or demonstrated progressive disease during primary therapy. A partial response was considered a 50% or greater reduction in the product obtained from measurement of each bi-dimensional lesion for at least 4 weeks or a decrease in the CA-125 level by at least 50% for at least 4 weeks. Disease progression was defined as a 50% or greater increase in the product from any lesion documented within 8 weeks of initiation of therapy, the appearance of any new lesion within 8 weeks of initiation of therapy, or any increase in the CA-125 from baseline at initiation of therapy. Stable disease was defined as disease not meeting any of the above criteria. All tissues, acquired with Institutional Review Board approval, were processed as previously reported (Boren et al, 2009; Dressman et al, 2007). Microarray gene expression data (Affymetrix HG-U133A) were analyzed for 142 patients (114 samples previously reported (Dressman et al, 2007) and 28 Moffitt Cancer Center (MCC) samples; GEO accession number GSE23554).

2. Results

The workflow for this example is summarized in FIG. 1. The $IC_{50}$ values for 36 OVCA cell lines treated with increasing doses of carboplatin, cisplatin, paclitaxel, and carboplatin plus paclitaxel treatment (Table 1) were correlated with gene expression data for each drug (Pearson correlation coefficient, P<0.01). Treatment of OVCA cell lines with carboplatin revealed 1,201 genes whose differential expression correlated with carboplatin sensitivity (P<0.01). This gene list corresponded to 77 biological pathways identified by GeneGo MetaCore™ analysis (FIG. 2A). Cisplatin sensitivity correlated with the expression of 454 unique genes (P<0.01), corresponding to 68 pathways. Twenty-three of these pathways were also correlated with carboplatin sensitivity (FIG. 2A). Treatment with paclitaxel revealed 1,025 genes associated with OVCA paclitaxel sensitivity (P<0.01), representing 64 biological pathways (FIG. 2B). Pearson correlation of the $IC_{50}$ values and gene expression data for the OVCA cell lines treated with a combination of carboplatin and paclitaxel (20,000:1 molar ratio) revealed 1,049 differentially expressed genes (P<0.01) and 25 pathways (FIG. 2B-D).

To distinguish between pathways that are unique to the mechanism of action of each drug and pathways that are common determinants of OVCA sensitivity, pathways containing genes that were correlated with sensitivity to multiple drugs were identified. Of the 25 pathways linked to sensitivity to carboplatin-paclitaxel combination therapy and the 68 pathways linked to cisplatin sensitivity, only 3 were identified in both analyses: "Apoptosis and Survival/BAD Phosphorylation," "Role of APC in Cell Cycle Regulation" (where APC is anaphase-promoting complex) and "Transcription/CREB" (FIG. 2D). Eight pathways were specifically correlated with carboplatin sensitivity, regardless of whether paclitaxel was used (see FIG. 2C). Two pathways were specifically correlated with sensitivity to paclitaxel treatment in both the presence and absence of carboplatin (see FIG. 2B).

To further distinguish core pathways involved in the response to chemotherapeutic agents in OVCA, the union of three individual comparisons was analyzed: carboplatin sensitivity vs. cisplatin sensitivity, carboplatin-paclitaxel sensitivity vs. cisplatin sensitivity, and carboplatin-paclitaxel sensitivity vs. carboplatin sensitivity. Three pathways were identified with a shared role in OVCA sensitivity to carboplatin and cisplatin single-agent treatment and carboplatin and paclitaxel combination treatment: (1) "Apoptosis and Survival/BAD Phosphorylation," (2) "Role of APC in Cell Cycle Regulation," and (3) "Transcription/CREB" (FIG. 3). Diagrams of the genes/proteins involved in these pathways are provided in FIG. 3 (GeneGo MetaCore output).

A similar PCA analysis was performed using a set of 177 colon cancers (Smith et al., Gastroenterology 138:958-968 (2009), which is hereby incorporated by reference in its entirety and specifically for the description of the colon cancers). The CREB pathway was found to be correlated with clinical outcomes in colon cancer.

Figure 4A:
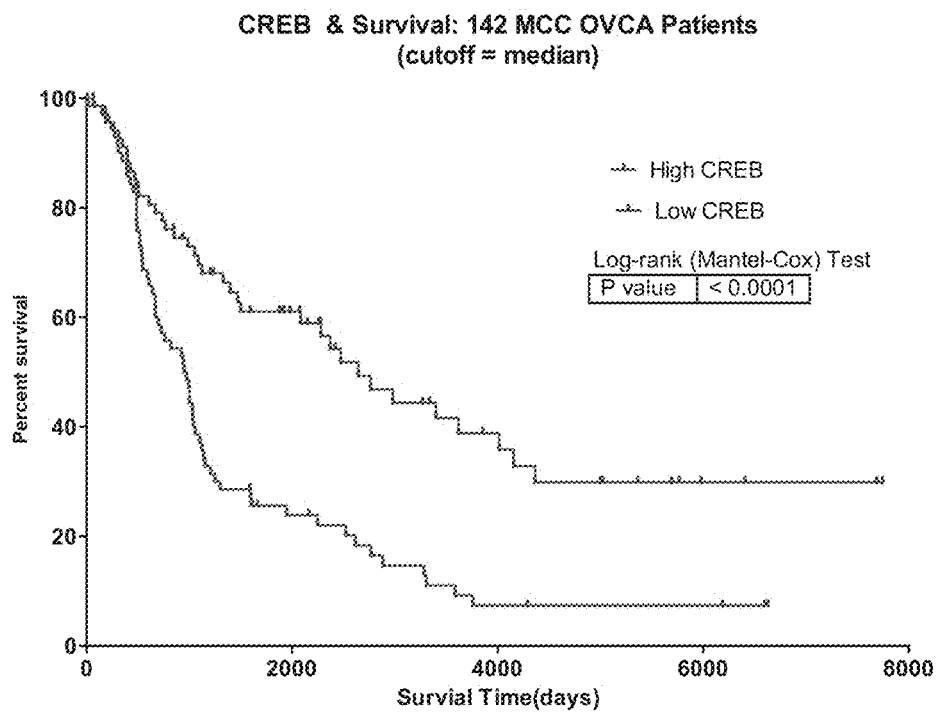
FIGS. 4A-4F are graphs showing low CREB pathway and high APC pathway signature PCA scores are associated with favorable clinical outcome. Kaplan-Meier curves depict the association between CREB-pathway signature PCA score (A-C) and APC-pathway signature PCA score (D-F) and overall survival from cancer for Moffitt and Duke datasets. ˆInformation available for 141 of 142 samples. Log-rank test P values indicate significance. CR: complete response; IR: incomplete response; O: optimal; S: suboptimal.
Figure 4B:
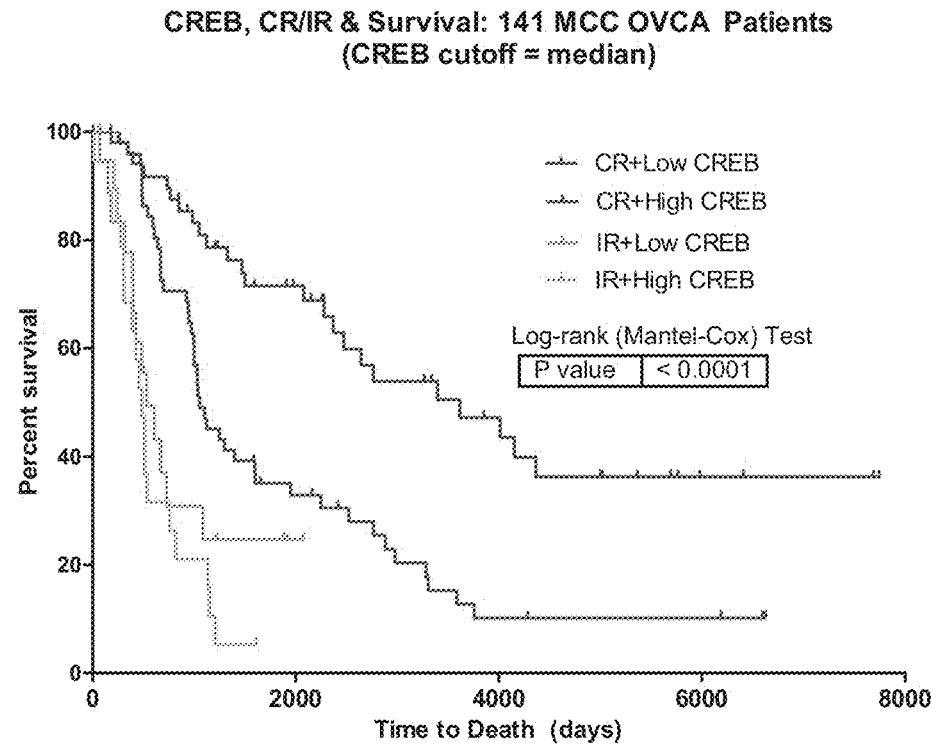
Figure 4C:
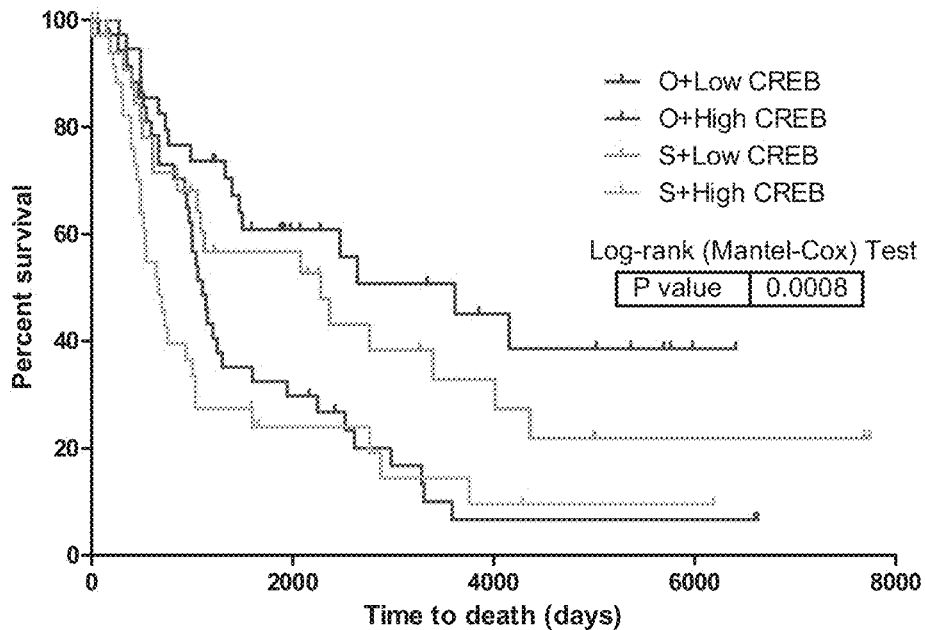

Based on the above data, PCA was used to develop expression signatures for both the Role of APC in Cell Cycle Regulation and the Transcription/CREB pathways. An Apoptosis and Survival/BAD Phosphorylation pathway signature and its associations with chemo-sensitivity and overall survival are described in Marchion 2011 and in PCT Application No. PCT/US2012/026617. A 55-gene APC in Cell Cycle Regulation pathway signature and a 103-gene Transcription/CREB pathway signature were generated and evaluated in an independent OVCA genomic dataset (Tables 2 and 3). Expression of the Transcription/CREB pathway gene signature was associated with overall survival from OVCA (n=142, P<0.0001; FIG. 4A). Furthermore, the OVCA genomic dataset was evaluated with regard to Transcription/CREB pathway gene expression signature score and surgical cytoreductive (debulking, n=141, with debulking status unavailable for 1 of 142 patients) status (optimal: <1 cm; suboptimal: >1 cm residual tumor at conclusion of surgery, P<0.001; FIG. 4C) and also response to primary platinum-based therapy (complete or incomplete response, P<0.0001; FIG. 4B). An association between low Transcription/CREB pathway gene expression signature score and favorable outcome was observed in patients who underwent optimal and suboptimal debulking (optimal: adjusted P=0.002, suboptimal: adjusted P=0.02). Most importantly, OVCA patients with a low Transcription/CREB pathway gene expression signature score who underwent suboptimal debulking had survival data that trended toward superiority versus patients with a high Transcription/CREB pathway gene expression signature score who underwent optimal debulking (adjusted P=0.08). Interestingly, patients who demonstrated a complete response to primary platinum-based therapy but had a low Transcription/CREB pathway gene expression signature score had notably superior survival than patients who demonstrated a complete response but had a high Transcription/CREB pathway gene expression signature score (adjusted P=0.0001). Patients who had an incomplete response to primary therapy had no difference in survival associated with their Transcription/CREB pathway gene expression signature score (P=0.27). When evaluated with debulking status and response to primary platinum-based therapy, grade, and age, the Cox proportional hazards multivariable model revealed that the Transcription/CREB pathway gene expression signature score was an independent variable associated with survival (P=0.01).

Figure 5:
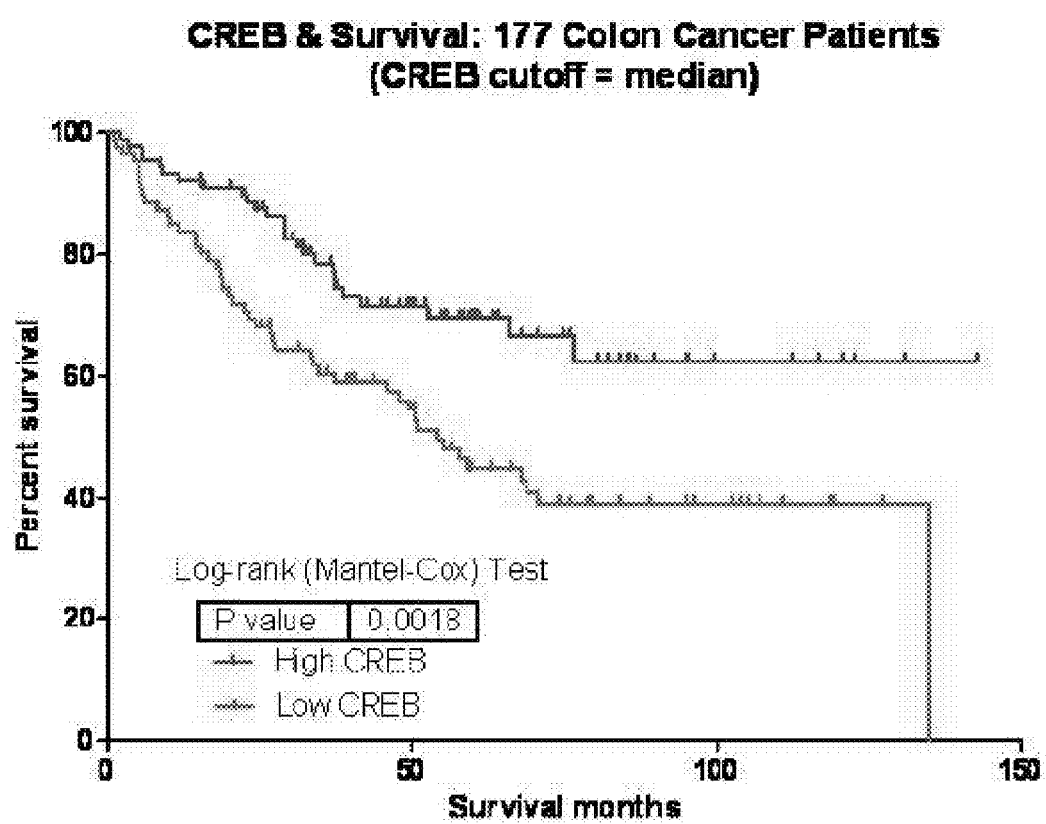
FIG. 5 is a graph showing high CREB pathway signature PCA scores are associated with favorable clinical outcome. Kaplan-Meier curves depict the association between CREB-pathway signature PCA score and overall survival from colon cancer. The curve to the right and bottom is low CREB and the curve to the left and top is high CREB.

Expression of the Transcription/CREB pathway gene signature was associated with overall survival from colon cancer (n=177, P≤0.0018; FIG. 5). A high CREB pathway gene expression signature score in colon cancer was correlated to more positive clinical outcomes. For example, overall survival was increased in colon cancer patients with a high CREB pathway gene expression signature score (FIG. 5).

Figure 4D:
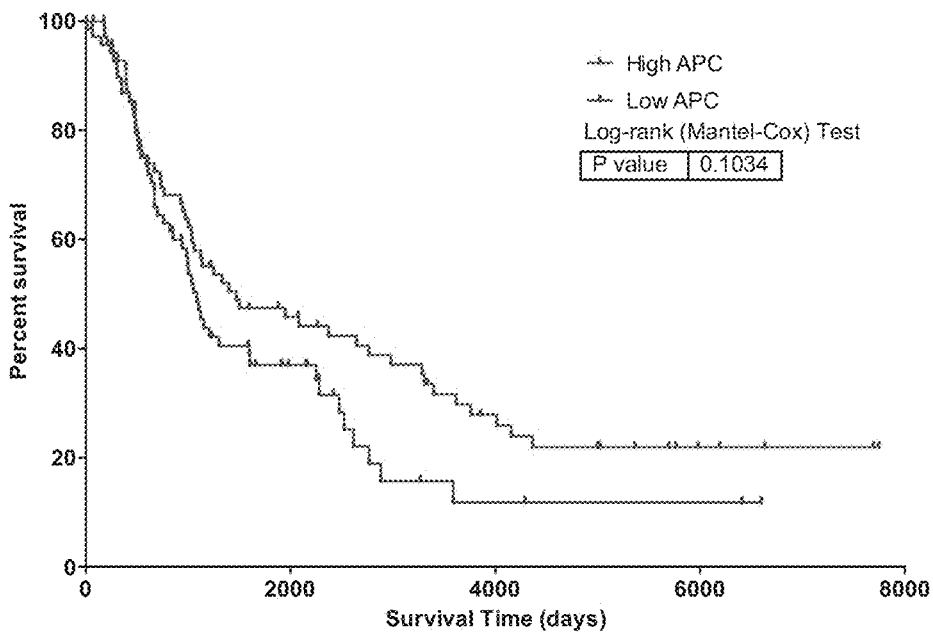
Figure 4E:
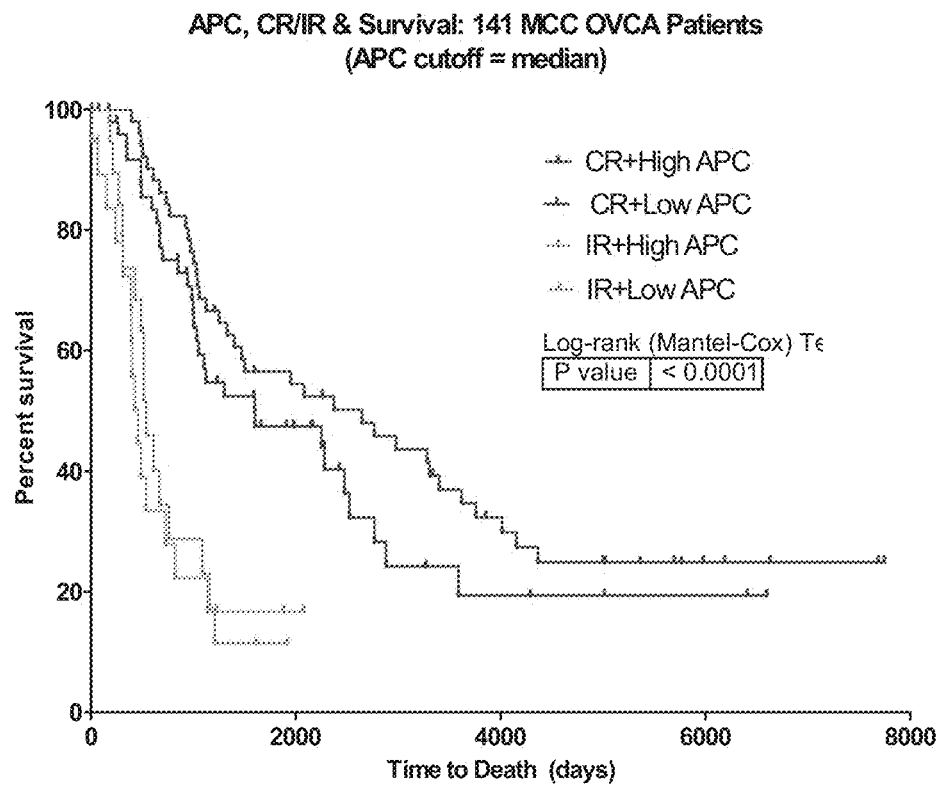
Figure 4F:
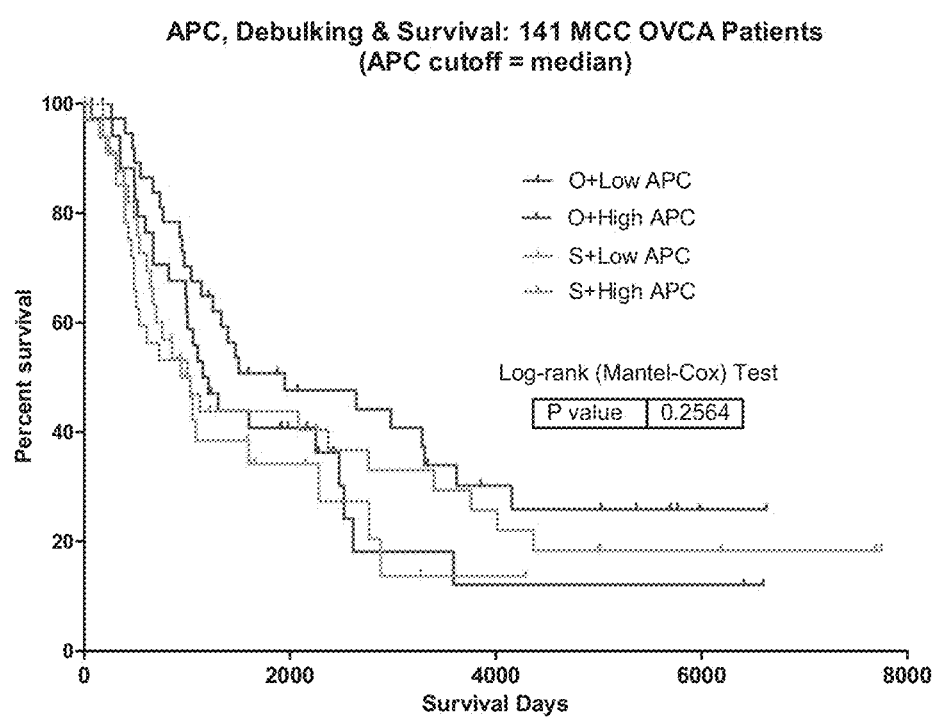

The Role of APC in Cell Cycle Regulation pathway gene expression signature score demonstrated a trend toward an association with overall survival from OVCA, although results did not reach statistical significance (n=142, P=0.1, FIG. 4D). No association between the Role of APC in Cell Cycle Regulation pathway gene expression signature score and survival was observed within the group of patients who had optimal (P=0.1384) or suboptimal (P=0.6192) cytoreductive surgery or who had demonstrated a complete (P=0.2154) or incomplete (P=0.6984) response to primary platinum-based therapy.

Cancer cells employ a variety of strategies to deregulate apoptosis, cell cycle progression, and cellular metabolism during the course of their evolution. (Hanahan & Weinberg) In this study, integration of OVCA cell line chemo-sensitivity and genome-wide expression data implicated pathways, which include BAD, APC, and CREB, as key mediators of sensitivity to chemotherapeutic agents, that, when deregulated, may contribute to the acquired drug resistance frequently observed in OVCA patients. Furthermore, when genome-wide expression results were integrated with clinical outcomes data from patients with advanced-stage OVCA, it was found that these pathways are not only associated with in vitro drug sensitivity but also with patient survival.

The primary finding was regarding the Transcription/CREB pathway. Expression of this pathway was significantly associated with survival in patients who demonstrate a complete response to primary platinum-based therapy (adjusted P=0.0001), suggesting that expression of this pathway not only influences OVCA response to platinum-based therapy but also to the behavior of de novo platinum-sensitive tumors subsequent to a complete response to primary therapy such that survival is impacted. No such effect was observed in patients who experience an incomplete response to platinum, suggesting that, although expression of the pathway is associated with primary chemosensitivity, it has no influence on the post-treatment phenotypic behavior of OVCAs that are resistant to platinum. Notably, the influence of the Transcription/CREB pathway on overall survival also approached statistical significance, despite cytoreductive status (the volume of residual disease at the completion of primary surgery), which is considered one of the most important clinical determinants of survival for patients with OVCA. Such findings could have substantial implications for future clinical treatment of patients with this disease, although additional studies are required.

CREB (cAMP response element binding protein) is a transcription factor that can be activated by multiple pathways that affect cellular cAMP levels, and its many targets play important roles in cellular metabolism, proliferation, and survival (Mayr & Montminy, 2001; Zhang et al, 2005). G-protein-coupled receptors, transmembrane proteins that transduce extracellular signals to intracellular effector pathways via heterotrimeric G proteins, activate the enzyme adenylate cyclase, which catalyzes the conversion of ATP to cAMP. cAMP then binds the regulatory subunits of protein kinase A (PKA), which leads to the release of the PKA catalytic subunits (Lappano & Maggiolini). Active PKA migrates to the nucleus, where it phosphorylates CREB (Gonzalez & Montminy, 1989). Phosphorylated CREB then binds its coactivator CBP/p300, a histone acetyltransferase, and together CREB and CBP/p300 activate the transcription of genes whose promoters contain a CRE (cAMP response element) sequence (Bannister & Kouzarides, 1996; Parker et al, 1996). CREB overexpression may be required for the proliferation and survival of human cancers (Bonni et al, 1999; Siu & Jin, 2007). Additionally, the CREB coactivator CBP/p300 is mutated in several human cancers, with loss of CBP/p300 histone acetyltransferase activity potentially impacting the expression of several tumor suppressor targets (Iyer et al, 2004).

The anaphase-promoting complex/cyclosome (APC/C) is a multi-subunit ubiquitin ligase required for regulation of cell cycle progression and mitotic exit. APC/C consists of multiple core subunits and an activator component. APC/C is tightly regulated during the cell cycle via the cyclical binding of the Cdc20 (cell division cycle 20) and Cdh1 (cell division cycle homolog 1) activating subunits. The major role of APC/C is to target substrates for proteasomal degradation in an orchestrated manner, with Cdc20 and Cdh1 mediating substrate recognition to ensure that mitotic entry and exit occur correctly. APC/C$^{Cdc20}$ is active from anaphase to the end of mitosis, and APC/C$^{Cdh1}$ is active from late mitosis to the $G_1$-S transition. APC/C$^{Cdc20}$-mediated destruction of targets such as securin and cyclin B drives chromosome separation and exit from mitosis. As mitotic cyclins are degraded, cyclin-dependent kinase activity decreases. By late M phase, Cdh1 is no longer phosphorylated and can bind to the core APC/C subunits. APC/C$^{Cdh1}$ has multiple targets, including Cdc20, mitotic cyclins, mitotic kinases, and inhibitors of DNA replication origin licensing. Collectively, degradation of APC/C$^{Cdh1}$ targets ensures that cells do not duplicate their DNA and/or enter mitosis prematurely (Nakayama & Nakayama, 2006). Because of the critical role of APC/C in regulating chromosome segregation during mitosis, deregulation of the complex could cause genomic instability and contribute to tumorigenesis. Indeed, loss of function mutations of core APC/C subunits has been observed in colorectal cancer cells, upregulation of Cdc20 has been observed in several human cancers, and loss of Cdh1 causes chromosomal instability and tumor formation in mice (Garcia-Higuera et al, 2008; Nakayama & Nakayama, 2006; Wang et al, 2003).

BAD (BCL-xL/BCL-2-associated death promoter) was first identified in a yeast two-hybrid screen for BCL-2 interactors (Yang et al, 1995). Heterodimerization between BAD and BCL-2, BCL-xL, or BCL-W promotes apoptosis through the displacement of BAK and BAX (Holmgreen et al, 1999; Yang et al, 1995). The interaction between BAD and its partners is dependent on the BAD BH3 domain (Zha et al, 1997). Upon apoptotic stimuli, BAD translocates from the cytosol to the mitochondria (Jia et al, 1999; Zha et al, 1996) where it neutralizes the anti-apoptotic proteins and promotes mitochondrial membrane permeabilization (Datta et al, 2000; Roy et al, 2009). Subversion of BAD-mediated apoptosis may thus be an important mechanism by which tumor cells acquire resistance to apoptotic stimuli. A role of BAD-induced apoptosis in tumor suppression is supported by the identification of BAD mutations in colon cancer that disrupt binding to BCL-2 and BCL-xL and the observation that BAD-deficient mice are prone to diffuse B cell lymphoma (Lee et al, 2004; Ranger et al, 2003). Furthermore, because post-translational modification of BAD represents a key control point between cell survival and apoptosis, BAD phosphorylation is frequently deregulated in cancer. Activation of multiple signaling pathways by growth factors, cytokines, or oncogenic mutations can contribute to increased BAD phosphorylation, with aberrant kinase and phosphatase activity leading to BAD inactivation and resistance to cell death signaling in tumors (Danial, 2008).

BAD, CREB, and APC/C may be linked by common signaling molecules, as signaling pathways converge in many ways to regulate cellular proliferation and survival at both the transcriptional and post-transcriptional levels. For example, PKA phosphorylation activates CREB and inactivates BAD and APC/C$^{Cdc20}$ (Gonzalez & Montminy, 1989; Harada et al, 2001; Lizcano et al, 2000; Searle et al, 2004). AKT also phosphorylates BAD and CREB, and AKT phosphorylation protects some APC/C$^{Cdh1}$ substrates from degradation (Datta et al, 1997; del Peso et al, 1997; Gao et al, 2009). PTEN can also promote the association between APC/C and Cdh1 to prevent S phase entry (Song et al). Cyclin-dependent kinases phosphorylate BAD, APC/C, and CBP/p300 (Ait-Si-Ali et al, 1998; Konishi et al, 2002; Zachariae et al, 1998). There may also be more direct crosstalk between BAD, CREB, and APC. BAD has been linked to regulation of cell cycle progression and has been found at CREs in cyclin genes (Chattopadhyay et al, 2001; Fernando et al, 2007). The APC/C subunits APC5 and APC7 directly bind CBP/p300, stimulate CBP/p300 histone acetyltransferase activity, and potentiate CBP/p300-dependent transcription (Turnell et al, 2005). CREB may also directly impact cell survival by binding to CREs in the promoters of anti-apoptotic factor genes such as BCL-2 to induce their transcription (Wilson et al, 1996).

Based on the known interactions between these proteins, BAD, APC/C, and CREB may interact in a common pathway to induce cell cycle arrest and death in response to mitotic or metabolic stress caused by carboplatin, cisplatin, and paclitaxel. Deregulation of components of these pathways may thus lead to acquired drug resistance. Indeed, abnormal cell cycle progression, defective apoptosis, and metabolic reprogramming have been implicated as key mechanisms of OVCA chemoresistance (Etemadmoghadam et al, 2009; Hajra et al, 2008; Montopoli et al; Takahashi et al, 2005).

As shown herein, integration of chemosensitivity and genome-wide expression data can provide a more comprehensive understanding of the mechanisms involved in drug responses. The results demonstrate that characterization of gene expression signatures in OVCA patients may be useful for characterizing responses to treatment and also in developing an understanding of the biology that drives clinical outcome and survival. Furthermore, the identification of BAD, APC/C, and CREB as key players in the cytotoxicity of carboplatin, cisplatin, and paclitaxel in OVCA cell lines suggests that targeted therapies against regulators of these proteins may be worthy of study in chemoresistant OVCAs.

TABLE 1

| Cell line | Cisplatin | | | | Carboplatin | | | |
|---|---|---|---|---|---|---|---|---|
| | IC50 mean | n | (SEM) | (RSE) | IC50 mean | n | (SEM) | (RSE) |
| A2008 | 1.5E−6 | 12 | 414.6E−9 | 27.9 | 20.2E−6 | 17 | 3.9E−6 | 19.3 |
| A2780CP | 43.8E−6 | 10 | 7.9E−6 | 18.1 | 94.2E−6 | 11 | 12.0E−6 | 12.7 |
| A2780S | 4.7E−6 | 13 | 1.8E−6 | 39.4 | 24.3E−6 | 14 | 7.2E−6 | 29.7 |
| BG1 | 36.4E−6 | 4 | 8.5E−6 | 23.4 | 144.4E−6 | 7 | 26.4E−6 | 18.3 |
| C13 | 17.9E−6 | 7 | 6.6E−6 | 36.9 | 56.8E−6 | 11 | 12.3E−6 | 21.6 |
| CAOV2 | 4.5E−6 | 8 | 2.1E−6 | 48.1 | 70.2E−6 | 19 | 15.7E−6 | 22.4 |
| CAOV3 | 34.4E−6 | 3 | 14.7E−6 | 42.7 | 69.4E−6 | 5 | 18.0E−6 | 25.9 |
| CHI | 4.9E−6 | 14 | 2.0E−6 | 41.1 | 23.6E−6 | 10 | 5.6E−6 | 23.6 |
| CHIcisR | 1.3E−6 | 14 | 244.3E−9 | 19.3 | 20.0E−6 | 9 | 5.6E−6 | 27.9 |
| Dov13 | 24.6E−6 | 4 | 11.9E−6 | 48.6 | 104.5E−6 | 10 | 30.6E−6 | 29.3 |
| FUOV1 | | | | | 87.9E−6 | 5 | 22.7E−6 | 25.9 |
| HeyA8 | 33.1E−6 | 3 | 26.0E−6 | 78.5 | 290.8E−6 | 8 | 34.5E−6 | 11.9 |
| IGR-OV1 | 1.4E−6 | 1 | | | 65.4E−6 | 3 | 26.2E−6 | 40.0 |
| IMCC3 | 22.0E−6 | 3 | 14.4E−6 | 65.4 | 69.5E−6 | 6 | 11.2E−6 | 16.1 |
| IMCC5 | 4.9E−6 | 9 | 1.5E−6 | 30.0 | 41.3E−6 | 4 | 8.1E−6 | 19.6 |
| M41 | 12.8E−6 | 4 | 4.7E−6 | 36.5 | 41.6E−6 | 10 | 10.8E−6 | 26.1 |
| M41CSR | 13.5E−6 | 4 | 3.5E−6 | 26.2 | 48.2E−6 | 7 | 9.9E−6 | 20.5 |
| MCAS | 61.3E−6 | 9 | 15.4E−6 | 25.1 | 237.0E−6 | 15 | 53.7E−6 | 22.7 |
| OV2008 | 3.5E−6 | 3 | 2.1E−6 | 58.7 | 45.1E−6 | 11 | 5.5E−6 | 12.1 |
| OV90 | | | | | 212.6E−6 | 7 | 27.1E−6 | 12.7 |
| Ovary1847 | 8.7E−6 | 3 | 6.9E−6 | 79.1 | 171.9E−6 | 3 | 35.2E−6 | 20.5 |
| OVCA420 | 13.7E−6 | 1 | | | 165.8E−6 | 5 | 14.8E−6 | 8.9 |
| OVCA429 | 5.8E−6 | 1 | | | 224.8E−6 | 5 | 39.5E−6 | 17.6 |
| OVCA432 | 1.4E−6 | 1 | | | 63.1E−6 | 5 | 5.2E−6 | 8.3 |
| OVCA433 | 8.8E−6 | 1 | | | 270.2E−6 | 6 | 56.2E−6 | 20.8 |
| OVCAR10 | 32.5E−6 | 3 | 12.4E−6 | 38.3 | 128.3E−6 | 1 | | |
| OVCAR2 | 3.7E−6 | 5 | 1.6E−6 | 44.8 | 45.5E−6 | 11 | 5.0E−6 | 11.0 |
| OVCAR3 | 1.3E−6 | 5 | 413.5E−9 | 31.9 | 83.7E−6 | 4 | 33.1E−6 | 39.5 |
| OVCAR4 | 20.5E−6 | 11 | 5.4E−6 | 26.3 | 72.0E−6 | 22 | 8.3E−6 | 11.6 |
| OVCAR5 | 12.9E−6 | 10 | 2.8E−6 | 21.4 | 125.2E−6 | 3 | 22.0E−6 | 17.6 |
| OVCAR8 | 75.3E−6 | 1 | | | 56.1E−6 | 5 | 2.3E−6 | 4.1 |
| SKOV3 | | | | | 247.4E−6 | 8 | 29.8E−6 | 12.0 |
| SK-OV-4 | 13.0E−6 | 7 | 5.6E−6 | 43.2 | 23.0E−6 | 11 | 3.2E−6 | 13.8 |
| TOV112D | | | | | 75.8E−6 | 7 | 16.4E−6 | 21.7 |
| Tyknu | 4.8E−6 | 3 | 315.8E−9 | 6.6 | 9.6E−6 | 7 | 1.8E−6 | 18.6 |
| TyknuCisR | 17.7E−6 | 4 | 5.7E−6 | 32.1 | 63.7E−6 | 7 | 20.0E−6 | 31.3 |

| Cell line | Paclitaxel | | | | Carboplatin + Paclitaxel | | | |
|---|---|---|---|---|---|---|---|---|
| | IC50 mean | n | (SEM) | (RSE) | IC50 mean | n | (SEM) | (RSE) |
| A2008 | 5.8E−9 | 6 | 2.6E−9 | 44.7 | 17.3E−6 | 24 | 1.3E−6 | 7.3 |
| A2780CP | 4.0E−9 | 8 | 1.5E−9 | 37.2 | 37.1E−6 | 15 | 4.8E−6 | 12.8 |
| A2780S | 2.4E−9 | 6 | 625.3E−12 | 25.7 | 18.1E−6 | 16 | 2.2E−6 | 12.1 |
| BG1 | 5.5E−9 | 7 | 717.7E−12 | 13.1 | 55.1E−6 | 19 | 3.3E−6 | 5.9 |
| C13 | 3.2E−9 | 10 | 751.1E−12 | 23.7 | 26.2E−6 | 16 | 3.5E−6 | 13.5 |
| CAOV2 | 20.4E−9 | 4 | 7.4E−9 | 36.4 | 72.3E−6 | 9 | 27.8E−6 | 38.5 |
| CAOV3 | 4.6E−9 | 5 | 1.1E−9 | 24.4 | 30.6E−6 | 15 | 2.8E−6 | 9.0 |
| CHI | 998.9E−12 | 5 | 284.0E−12 | 28.4 | 22.1E−6 | 14 | 3.5E−6 | 15.7 |
| CHIcisR | 1.8E−9 | 4 | 280.5E−12 | 15.8 | 12.3E−6 | 20 | 1.2E−6 | 10.1 |
| Dov13 | 17.3E−9 | 4 | 4.6E−9 | 26.8 | 47.2E−6 | 3 | 1.8E−6 | 3.7 |
| FUOV1 | 4.4E−6 | 3 | 3.5E−6 | 80.9 | 64.3E−6 | 16 | 10.4E−6 | 16.2 |
| HeyA8 | 17.4E−9 | 5 | 3.1E−9 | 17.9 | 153.7E−6 | 4 | 24.0E−6 | 15.6 |
| IGR-OV1 | 37.4E−9 | 3 | 21.5E−9 | 57.4 | 38.5E−6 | 10 | 8.6E−6 | 22.5 |
| IMCC3 | | | | | 52.4E−6 | 3 | 25.8E−6 | 49.2 |
| IMCC5 | 3.1E−9 | 4 | 861.1E−12 | 28.0 | 23.1E−6 | 23 | 3.6E−6 | 15.6 |
| M41 | 6.3E−9 | 5 | 1.2E−9 | 18.8 | 28.2E−6 | 4 | 2.4E−6 | 8.6 |

TABLE 1-continued

| | | | | | | | | |
|---|---|---|---|---|---|---|---|---|
| M41CSR | 2.5E−9 | 7 | 557.3E−12 | 22.7 | 32.0E−6 | 19 | 1.6E−6 | 5.1 |
| MCAS | 2.9E−9 | 3 | 880.5E−12 | 30.8 | 96.8E−6 | 11 | 39.7E−6 | 41.0 |
| OV2008 | 13.9E−9 | 8 | 5.7E−9 | 41.0 | 43.3E−6 | 44 | 3.0E−6 | 7.0 |
| OV90 | 107.8E−9 | 6 | 52.7E−9 | 48.9 | 59.5E−6 | 23 | 6.4E−6 | 10.7 |
| Ovary1847 | 5.6E−9 | 3 | 3.4E−9 | 61.4 | 39.9E−6 | 10 | 2.8E−6 | 7.1 |
| OVCA420 | | | | | 133.4E−6 | 9 | 11.0E−6 | 8.2 |
| OVCA429 | 2.9E−9 | 7 | 550.1E−12 | 18.8 | 47.6E−6 | 18 | 3.0E−6 | 6.4 |
| OVCA432 | 6.3E−9 | 6 | 541.2E−12 | 8.6 | 45.0E−6 | 16 | 4.4E−6 | 9.7 |
| OVCA433 | 2.1E−9 | 7 | 464.1E−12 | 21.9 | 47.9E−6 | 16 | 5.3E−6 | 11.1 |
| OVCAR10 | 7.1E−9 | 2 | 2.0E−9 | 27.7 | 37.5E−6 | 12 | 7.9E−6 | 21.0 |
| OVCAR2 | 2.8E−9 | 8 | 566.7E−12 | 20.4 | 30.2E−6 | 41 | 1.6E−6 | 5.3 |
| OVCAR3 | 16.9E−9 | 4 | 12.1E−9 | 71.6 | 45.6E−6 | 10 | 3.6E−6 | 7.9 |
| OVCAR4 | 17.8E−9 | 3 | 9.6E−9 | 53.8 | 62.2E−6 | 11 | 12.5E−6 | 20.0 |
| OVCAR5 | 5.6E−9 | 4 | 577.1E−12 | 10.3 | 59.6E−6 | 24 | 5.3E−6 | 8.9 |
| OVCAR8 | 5.7E−9 | 2 | 935.0E−12 | 16.4 | 51.8E−6 | 34 | 2.9E−6 | 5.5 |
| SKOV3 | 88.7E−9 | 6 | 55.3E−9 | 62.4 | 52.7E−6 | 22 | 6.3E−6 | 11.9 |
| SK-OV-4 | 2.3E−9 | 9 | 346.4E−12 | 15.2 | 18.8E−6 | 41 | 1.2E−6 | 6.6 |
| TOV112D | 110.7E−9 | 5 | 66.1E−9 | 59.7 | 38.9E−6 | 23 | 6.4E−6 | 16.4 |
| Tyknu | 8.3E−9 | 4 | 2.4E−9 | 29.2 | 10.5E−6 | 3 | 1.5E−6 | 14.2 |
| TyknuCisR | 7.2E−9 | 7 | 1.3E−9 | 17.9 | 47.5E−6 | 20 | 2.8E−6 | 5.9 |

TABLE 2

APC/cell cycle regulation

| Probe Set ID | Gene Description | Gene Symbol |
|---|---|---|
| 1554768_a_at | MAD2 mitotic arrest deficient-like 1 (yeast) | MAD2L1 |
| 1555772_a_at | cell division cycle 25 homolog A (*S. pombe*) | CDC25A |
| 1560161_at | Cyclin B2 | CCNB2 |
| 200098_s_at | anaphase promoting complex subunit 5 | ANAPC5 |
| 200812_at | chaperonin containing TCP1, subunit 7 (eta) | CCT7 |
| 200873_s_at | chaperonin containing TCP1, subunit 8 (theta) | CCT8 |
| 200877_at | chaperonin containing TCP1, subunit 4 (delta) | CCT4 |
| 200910_at | chaperonin containing TCP1, subunit 3 (gamma) | CCT3 |
| 201326_at | chaperonin containing TCP1, subunit 6A (zeta 1) | CCT6A |
| 201327_s_at | chaperonin containing TCP1, subunit 6A (zeta 1) | CCT6A |
| 201429_s_at | polo-like kinase 1 (*Drosophila*) /// ribosomal protein L37a | PLK1 /// RPL37A |
| 201456_s_at | BUB3 budding uninhibited by benzimidazoles 3 homolog (yeast) | BUB3 |
| 201457_x_at | BUB3 budding uninhibited by benzimidazoles 3 homolog (yeast) | BUB3 |
| 201458_s_at | BUB3 budding uninhibited by benzimidazoles 3 homolog (yeast) | BUB3 |
| 201897_s_at | CDC28 protein kinase regulatory subunit 1B | CKS1B |
| 201946_s_at | chaperonin containing TCP1, subunit 2 (beta) | CCT2 |
| 201947_s_at | chaperonin containing TCP1, subunit 2 (beta) | CCT2 |
| 202183_s_at | kinesin family member 22 /// similar to Kinesin-like protein KIF22 (Kinesin-like DNA-binding protein) (Kinesin-like protein 4) | KIF22 /// LOC728037 |
| 202240_at | polo-like kinase 1 (*Drosophila*) | PLK1 |
| 202705_at | cyclin B2 | CCNB2 |
| 202717_s_at | cell division cycle 16 homolog (*S. cerevisiae*) | CDC16 |
| 202741_at | protein kinase, cAMP-dependent, catalytic, beta | PRKACB |
| 202742_s_at | protein kinase, cAMP-dependent, catalytic, beta | PRKACB |
| 202801_at | protein kinase, cAMP-dependent, catalytic, alpha | PRKACA |
| 202870_s_at | cell division cycle 20 homolog (*S. cerevisiae*) | CDC20 |
| 202892_at | cell division cycle 23 homolog (*S. cerevisiae*) | CDC23 |
| 203213_at | cell division cycle 2, G1 to S and G2 to M | CDC2 |
| 203214_x_at | cell division cycle 2, G1 to S and G2 to M | CDC2 |
| 203362_s_at | MAD2 mitotic arrest deficient-like 1 (yeast) | MAD2L1 |
| 203418_at | cyclin A2 | CCNA2 |
| 203554_x_at | pituitary tumor-transforming 1 | PTTG1 |
| 203625_x_at | melanoma cell adhesion molecule | MCAM |
| 203626_s_at | S-phase kinase-associated protein 2 (p45) | SKP2 |
| 203755_at | BUB1 budding uninhibited by benzimidazoles 1 homolog beta (yeast) | BUB1B |
| 203967_at | cell division cycle 6 homolog (*S. cerevisiae*) | CDC6 |
| 203968_s_at | cell division cycle 6 homolog (*S. cerevisiae*) | CDC6 |
| 204092_s_at | aurora kinase A | AURKA |
| 204252_at | cyclin-dependent kinase 2 | CDK2 |
| 204346_s_at | Ras association (RalGDS/AF-6) domain family 1 | RASSF1 |
| 204641_at | NIMA (never in mitosis gene a)-related kinase 2 | NEK2 |
| 204695_at | cell division cycle 25 homolog A (*S. pombe*) | CDC25A |
| 204696_s_at | cell division cycle 25 homolog A (*S. pombe*) | CDC25A |
| 205085_at | origin recognition complex, subunit 1-like (yeast) | ORC1L |
| 205288_at | CDC14 cell division cycle 14 homolog A (*S. cerevisiae*) | CDC14A |
| 205899_at | cyclin A1 | CCNA1 |
| 206587_at | chaperonin containing TCP1, subunit 6B (zeta 2) | CCT6B |
| 207228_at | protein kinase, cAMP-dependent, catalytic, gamma | PRKACG |
| 207845_s_at | anaphase promoting complex subunit 10 | ANAPC10 |

TABLE 2-continued

APC/cell cycle regulation

| Probe Set ID | Gene Description | Gene Symbol |
| --- | --- | --- |
| 208079_s_at | aurora kinase A | AURKA |
| 208080_at | aurora kinase A | AURKA |
| 208696_at | chaperonin containing TCP1, subunit 5 (epsilon) | CCT5 |
| 208721_s_at | anaphase promoting complex subunit 5 | ANAPC5 |
| 208722_s_at | anaphase promoting complex subunit 5 | ANAPC5 |
| 208722_s_at | anaphase promoting complex subunit 5 | ANAPC5 |
| 208778_s_at | t-complex 1 | TCP1 |
| 209001_s_at | anaphase promoting complex subunit 13 | ANAPC13 |
| 209414_at | fizzy/cell division cycle 20 related 1 (*Drosophila*) | FZR1 |
| 209415_at | fizzy/cell division cycle 20 related 1 (*Drosophila*) | FZR1 |
| 209416_s_at | fizzy/cell division cycle 20 related 1 (*Drosophila*) | FZR1 |
| 209464_at | aurora kinase B | AURKB |
| 209642_at | BUB1 budding uninhibited by benzimidazoles 1 homolog (yeast) | BUB1 |
| 209658_at | cell division cycle 16 homolog (*S. cerevisiae*) | CDC16 |
| 209659_s_at | cell division cycle 16 homolog (*S. cerevisiae*) | CDC16 |
| 209974_s_at | BUB3 budding uninhibited by benzimidazoles 3 homolog (yeast) | BUB3 |
| 210436_at | chaperonin containing TCP1, subunit 8 (theta) | CCT8 |
| 210440_s_at | CDC14 cell division cycle 14 homolog A (*S. cerevisiae*) | CDC14A |
| 210441_at | CDC14 cell division cycle 14 homolog A (*S. cerevisiae*) | CDC14A |
| 210559_s_at | cell division cycle 2, G1 to S and G2 to M | CDC2 |
| 210567_s_at | S-phase kinase-associated protein 2 (p45) | SKP2 |
| 210742_at | CDC14 cell division cycle 14 homolog A (*S. cerevisiae*) | CDC14A |
| 210743_s_at | CDC14 cell division cycle 14 homolog A (*S. cerevisiae*) | CDC14A |
| 211036_x_at | anaphase promoting complex subunit 5 | ANAPC5 |
| 211080_s_at | NIMA (never in mitosis gene a)-related kinase 2 | NEK2 |
| 211803_at | cyclin-dependent kinase 2 | CDK2 |
| 211804_s_at | cyclin-dependent kinase 2 | CDK2 |
| 211865_s_at | fizzy/cell division cycle 20 related 1 (*Drosophila*) | FZR1 |
| 213226_at | cyclin A2 | CCNA2 |
| 214236_at | Cell division cycle 27 homolog (*S. cerevisiae*) | CDC27 |
| 214710_s_at | cyclin B1 | CCNB1 |
| 215282_at | anaphase promoting complex subunit 13 | ANAPC13 |
| 215508_at | BUB1 budding uninhibited by benzimidazoles 1 homolog (yeast) | BUB1 |
| 215509_s_at | BUB1 budding uninhibited by benzimidazoles 1 homolog (yeast) | BUB1 |
| 216234_s_at | protein kinase, cAMP-dependent, catalytic, alpha /// similar to protein kinase, cAMP-dependent, catalytic, gamma | LOC730418 /// PRKACA |
| 216275_at | BUB1 budding uninhibited by benzimidazoles 1 homolog (yeast) | BUB1 |
| 216277_at | BUB1 budding uninhibited by benzimidazoles 1 homolog (yeast) | BUB1 |
| 216969_s_at | kinesin family member 22 /// similar to Kinesin-like protein KIF22 (Kinesin-like DNA-binding protein) (Kinesin-like protein 4) | KIF22 /// LOC728037 |
| 217878_s_at | cell division cycle 27 homolog (*S. cerevisiae*) | CDC27 |
| 217879_at | cell division cycle 27 homolog (*S. cerevisiae*) | CDC27 |
| 217880_at | Full-length cDNA clone CS0DF026YC07 of Fetal brain of *Homo sapiens* (human) | — |
| 217881_s_at | cell division cycle 27 homolog (*S. cerevisiae*) | CDC27 |
| 218350_s_at | geminin, DNA replication inhibitor | GMNN |
| 218555_at | anaphase promoting complex subunit 2 | ANAPC2 |
| 218875_s_at | F-box protein 5 | FBXO5 |
| 221436_s_at | cell division cycle associated 3 | CDCA3 |
| 222010_at | t-complex 1 | TCP1 |
| 222011_s_at | t-complex 1 | TCP1 |
| 223234_at | MAD2 mitotic arrest deficient-like 2 (yeast) | MAD2L2 |
| 223307_at | cell division cycle associated 3 | CDCA3 |
| 223651_x_at | cell division cycle 23 homolog (*S. cerevisiae*) | CDC23 |
| 224010_at | APC11 anaphase promoting complex subunit 11 homolog (yeast) | ANAPC11 |
| 225422_at | cell division cycle 26 homolog (*S. cerevisiae*) | CDC26 |
| 225521_at | anaphase promoting complex subunit 7 | ANAPC7 |
| 225554_s_at | anaphase promoting complex subunit 7 | ANAPC7 |
| 225554_s_at | anaphase promoting complex subunit 7 | ANAPC7 |
| 226414_s_at | APC11 anaphase promoting complex subunit 11 homolog (yeast) /// similar to APC11 anaphase promoting complex subunit 11 isoform 2 | ANAPC11 /// LOC728919 |
| 226917_s_at | anaphase promoting complex subunit 4 | ANAPC4 |
| 227171_at | — | — |
| 228729_at | cyclin B1 | CCNB1 |
| 229068_at | chaperonin containing TCP1, subunit 5 (epsilon) | CCT5 |
| 229827_at | BUB3 budding uninhibited by benzimidazoles 3 homolog (yeast) | BUB3 |
| 231481_at | cyclin B3 | CCNB3 |
| 231534_at | Cell division cycle 2, G1 to S and G2 to M | CDC2 |
| 232524_x_at | anaphase promoting complex subunit 4 | ANAPC4 |
| 232764_at | Cyclin B2 | CCNB2 |
| 232768_at | Cyclin B2 | CCNB2 |
| 234863_x_at | F-box protein 5 | FBXO5 |
| 235780_at | protein kinase, cAMP-dependent, catalytic, beta | PRKACB |
| 239219_at | aurora kinase B | AURKB |
| 239651_at | anaphase promoting complex subunit 5 | ANAPC5 |
| 240278_at | Ras association (RalGDS/AF-6) domain family 1 | RASSF1 |

TABLE 2-continued

| APC/cell cycle regulation | | |
|---|---|---|
| Probe Set ID | Gene Description | Gene Symbol |
| 241959_at | anaphase promoting complex subunit 10 /// similar to Anaphase-promoting complex subunit 10 (APC10) (Cyclosome subunit 10) | ANAPC10 /// LOC729198 /// LOC731853 |

TABLE 3

| CREB transcription control | | |
|---|---|---|
| Probe Set ID | Gene Description | Gene Symbol |
| 1552263_at | mitogen-activated protein kinase 1 | MAPK1 |
| 1552264_a_at | mitogen-activated protein kinase 1 | MAPK1 |
| 1552602_at | calcium channel, voltage-dependent, gamma subunit 5 | CACNG5 |
| 1552857_a_at | 5-hydroxytryptamine (serotonin) receptor 6 | HTR6 |
| 1552863_a_at | calcium channel, voltage-dependent, gamma subunit 6 | CACNG6 |
| 1554319_at | ribosomal protein S6 kinase, 90 kDa, polypeptide 5 | RPS6KA5 |
| 1555098_a_at | calcium channel, voltage-dependent, beta 2 subunit | CACNB2 |
| 1555694_a_at | Kv channel interacting protein 3, calsenilin | KCNIP3 |
| 1556340_at | Mitogen-activated protein kinase 12 | MAPK12 |
| 1556341_s_at | Mitogen-activated protein kinase 12 | MAPK12 |
| 1557354_at | Son of sevenless homolog 1 (Drosophila) | SOS1 |
| 1557675_at | V-raf-1 murine leukemia viral oncogene homolog 1 | RAF1 |
| 1557970_s_at | ribosomal protein S6 kinase, 90 kDa, polypeptide 2 | RPS6KA2 |
| 1558944_at | Calcium channel, voltage-dependent, P/Q type, alpha 1A subunit | CACNA1A |
| 1558945_s_at | Calcium channel, voltage-dependent, P/Q type, alpha 1A subunit | CACNA1A |
| 1558984_at | mitogen-activated protein kinase kinase kinase 11 | MAP3K11 |
| 1559419_at | calcium channel, voltage-dependent, beta 2 subunit | CACNB2 |
| 1559420_x_at | calcium channel, voltage-dependent, beta 2 subunit | CACNB2 |
| 1560074_at | protein kinase C, alpha | PRKCA |
| 1560689_s_at | V-akt murine thymoma viral oncogene homolog 2 | AKT2 |
| 1563431_x_at | Calmodulin 3 (phosphorylase kinase, delta) | CALM3 |
| 1567457_at | Ras-related C3 botulinum toxin substrate 1 (rho family, small GTP binding protein Rac1) | RAC1 |
| 1567458_s_at | ras-related C3 botulinum toxin substrate 1 (rho family, small GTP binding protein Rac1) | RAC1 |
| 1568629_s_at | phosphoinositide-3-kinase, regulatory subunit 2 (p85 beta) | PIK3R2 |
| 1569355_at | Kv channel interacting protein 3, calsenilin | KCNIP3 |
| 200603_at | protein kinase, cAMP-dependent, regulatory, type I, alpha (tissue specific extinguisher 1) | PRKAR1A |
| 200604_s_at | protein kinase, cAMP-dependent, regulatory, type I, alpha (tissue specific extinguisher 1) | PRKAR1A |
| 200605_s_at | protein kinase, cAMP-dependent, regulatory, type I, alpha (tissue specific extinguisher 1) | PRKAR1A |
| 200622_x_at | calmodulin 3 (phosphorylase kinase, delta) | CALM3 |
| 200623_s_at | calmodulin 3 (phosphorylase kinase, delta) | CALM3 |
| 200650_s_at | lactate dehydrogenase A | LDHA |
| 200653_s_at | calmodulin 1 (phosphorylase kinase, delta) | CALM1 |
| 200655_s_at | calmodulin 1 (phosphorylase kinase, delta) | CALM1 |
| 200726_at | protein phosphatase 1, catalytic subunit, gamma isoform | PPP1CC |
| 200780_x_at | GNAS complex locus | GNAS |
| 200846_s_at | protein phosphatase 1, catalytic subunit, alpha isoform | PPP1CA |
| 200981_x_at | GNAS complex locus | GNAS |
| 201244_s_at | v-raf-1 murine leukemia viral oncogene homolog 1 | RAF1 |
| 201374_x_at | protein phosphatase 2 (formerly 2A), catalytic subunit, beta isoform | PPP2CB |
| 201375_s_at | protein phosphatase 2 (formerly 2A), catalytic subunit, beta isoform | PPP2CB |
| 201407_s_at | protein phosphatase 1, catalytic subunit, beta isoform | PPP1CB |
| 201408_at | protein phosphatase 1, catalytic subunit, beta isoform | PPP1CB |
| 201409_s_at | protein phosphatase 1, catalytic subunit, beta isoform | PPP1CB |
| 201469_s_at | SHC (Src homology 2 domain containing) transforming protein 1 | SHC1 |
| 202530_at | mitogen-activated protein kinase 14 | MAPK14 |
| 202670_at | mitogen-activated protein kinase kinase 1 | MAP2K1 |
| 202741_at | protein kinase, cAMP-dependent, catalytic, beta | PRKACB |
| 202741_at | protein kinase, cAMP-dependent, catalytic, beta | PRKACB |
| 202742_s_at | protein kinase, cAMP-dependent, catalytic, beta | PRKACB |
| 202743_at | phosphoinositide-3-kinase, regulatory subunit 3 (p55, gamma) | PIK3R3 |
| 202801_at | protein kinase, cAMP-dependent, catalytic, alpha | PRKACA |
| 203379_at | ribosomal protein S6 kinase, 90 kDa, polypeptide 1 | RPS6KA1 |
| 203627_at | insulin-like growth factor 1 receptor | IGF1R |
| 203628_at | insulin-like growth factor 1 receptor | IGF1R |
| 203652_at | mitogen-activated protein kinase kinase kinase 11 | MAP3K11 |
| 203680_at | protein kinase, cAMP-dependent, regulatory, type II, beta | PRKAR2B |
| 203808_at | — | — |
| 203809_s_at | v-akt murine thymoma viral oncogene homolog 2 | AKT2 |

TABLE 3-continued

CREB transcription control

| Probe Set ID | Gene Description | Gene Symbol |
|---|---|---|
| 203843_at | ribosomal protein S6 kinase, 90 kDa, polypeptide 3 | RPS6KA3 |
| 203879_at | phosphoinositide-3-kinase, catalytic, delta polypeptide | PIK3CD |
| 204154_at | cysteine dioxygenase, type I | CDO1 |
| 204312_x_at | cAMP responsive element binding protein 1 | CREB1 |
| 204313_s_at | cAMP responsive element binding protein 1 | CREB1 |
| 204314_s_at | cAMP responsive element binding protein 1 | CREB1 |
| 204369_at | phosphoinositide-3-kinase, catalytic, alpha polypeptide | PIK3CA |
| 204524_at | 3-phosphoinositide dependent protein kinase-1 | PDPK1 |
| 204632_at | ribosomal protein S6 kinase, 90 kDa, polypeptide 4 | RPS6KA4 |
| 204633_s_at | ribosomal protein S6 kinase, 90 kDa, polypeptide 5 | RPS6KA5 |
| 204635_at | ribosomal protein S6 kinase, 90 kDa, polypeptide 5 | RPS6KA5 |
| 204686_at | insulin receptor substrate 1 | IRS1 |
| 204811_s_at | calcium channel, voltage-dependent, alpha 2/delta subunit 2 | CACNA2D2 |
| 204842_x_at | protein kinase, cAMP-dependent, regulatory, type II, alpha | PRKAR2A |
| 204843_s_at | protein kinase, cAMP-dependent, regulatory, type II, alpha | PRKAR2A |
| 204906_at | ribosomal protein S6 kinase, 90 kDa, polypeptide 2 | RPS6KA2 |
| 205579_at | histamine receptor H1 | HRH1 |
| 205580_s_at | histamine receptor H1 | HRH1 |
| 205802_at | transient receptor potential cation channel, subfamily C, member 1 | TRPC1 |
| 205803_s_at | transient receptor potential cation channel, subfamily C, member 1 | TRPC1 |
| 205845_at | calcium channel, voltage-dependent, T type, alpha 1H subunit | CACNA1H |
| 206024_at | 4-hydroxyphenylpyruvate dioxygenase | HPD |
| 206040_s_at | mitogen-activated protein kinase 11 | MAPK11 |
| 206106_at | mitogen-activated protein kinase 12 | MAPK12 |
| 206170_at | adrenergic, beta-2-, receptor, surface | ADRB2 |
| 206270_at | protein kinase C, gamma | PRKCG |
| 206384_at | calcium channel, voltage-dependent, gamma subunit 3 | CACNG3 |
| 206399_x_at | calcium channel, voltage-dependent, P/Q type, alpha 1A subunit | CACNA1A |
| 206425_s_at | transient receptor potential cation channel, subfamily C, member 3 | TRPC3 |
| 206612_at | calcium channel, voltage-dependent, gamma subunit 1 | CACNG1 |
| 206803_at | prodynorphin | PDYN |
| 206812_at | adrenergic, beta-3-, receptor | ADRB3 |
| 206923_at | protein kinase C, alpha | PRKCA |
| 206944_at | 5-hydroxytryptamine (serotonin) receptor 6 | HTR6 |
| 206996_x_at | calcium channel, voltage-dependent, beta 1 subunit | CACNB1 |
| 207050_at | calcium channel, voltage-dependent, alpha 2/delta subunit 1 | CACNA2D1 |
| 207105_s_at | phosphoinositide-3-kinase, regulatory subunit 2 (p85 beta) | PIK3R2 |
| 207162_at | calcium channel, voltage-dependent, N type, alpha 1B subunit | CACNA1B |
| 207163_s_at | v-akt murine thymoma viral oncogene homolog 1 | AKT1 |
| 207228_at | protein kinase, cAMP-dependent, catalytic, gamma | PRKACG |
| 207243_s_at | calmodulin 2 (phosphorylase kinase, delta) | CALM2 |
| 207577_at | 5-hydroxytryptamine (serotonin) receptor 4 | HTR4 |
| 207578_s_at | 5-hydroxytryptamine (serotonin) receptor 4 | HTR4 |
| 207613_s_at | calcium/calmodulin-dependent protein kinase (CaM kinase) II alpha | CAMK2A |
| 207693_at | calcium channel, voltage-dependent, beta 4 subunit | CACNB4 |
| 207776_s_at | calcium channel, voltage-dependent, beta 2 subunit | CACNB2 |
| 207818_s_at | 5-hydroxytryptamine (serotonin) receptor 7 (adenylate cyclase-coupled) | HTR7 |
| 207869_s_at | calcium channel, voltage-dependent, T type, alpha 1G subunit | CACNA1G |
| 207927_at | 5-hydroxytryptamine (serotonin) receptor 7 (adenylate cyclase-coupled) | HTR7 |
| 207957_s_at | Protein kinase C, beta 1 | PRKCB1 |
| 207998_s_at | calcium channel, voltage-dependent, L type, alpha 1D subunit | CACNA1D |
| 208020_s_at | calcium channel, voltage-dependent, L type, alpha 1C subunit | CACNA1C |
| 208214_at | adrenergic, beta-1-, receptor | ADRB1 |
| 208299_at | calcium channel, voltage-dependent, T type, alpha 1I subunit | CACNA1I |
| 208351_s_at | mitogen-activated protein kinase 1 | MAPK1 |
| 208377_s_at | calcium channel, voltage-dependent, L type, alpha 1F subunit | CACNA1F |
| 208432_s_at | calcium channel, voltage-dependent, R type, alpha 1E subunit | CACNA1E |
| 208441_at | insulin-like growth factor 1 receptor | IGF1R |
| 208486_at | dopamine receptor D5 | DRD5 |
| 208640_at | ras-related C3 botulinum toxin substrate 1 (rho family, small GTP binding protein Rac1) | RAC1 |
| 208641_s_at | ras-related C3 botulinum toxin substrate 1 (rho family, small GTP binding protein Rac1) | RAC1 |
| 208652_at | protein phosphatase 2 (formerly 2A), catalytic subunit, alpha isoform | PPP2CA |
| 208711_s_at | cyclinD1 | CCND1 |
| 208712_at | cyclinD1 | CCND1 |
| 209530_at | calcium channel, voltage-dependent, beta 3 subunit | CACNB3 |
| 209563_x_at | calmodulin 1 (phosphorylase kinase, delta) | CALM1 |
| 209685_s_at | protein kinase C, beta 1 | PRKCB1 |
| 209956_s_at | calcium/calmodulin-dependent protein kinase (CaM kinase) II beta | CAMK2B |
| 210058_at | mitogen-activated protein kinase 13 | MAPK13 |
| 210059_s_at | mitogen-activated protein kinase 13 | MAPK13 |
| 210108_at | — | — |
| 210185_at | calcium channel, voltage-dependent, beta 1 subunit | CACNB1 |
| 210349_at | calcium/calmodulin-dependent protein kinase IV | CAMK4 |
| 210380_s_at | calcium channel, voltage-dependent, T type, alpha 1G subunit | CACNA1G |

TABLE 3-continued

CREB transcription control

| Probe Set ID | Gene Description | Gene Symbol |
| --- | --- | --- |
| 210404_x_at | calcium/calmodulin-dependent protein kinase (CaM kinase) II beta | CAMK2B |
| 210449_x_at | mitogen-activated protein kinase 14 | MAPK14 |
| 210770_s_at | calcium channel, voltage-dependent, P/Q type, alpha 1A subunit | CACNA1A |
| 210814_at | transient receptor potential cation channel, subfamily C, member 3 | TRPC3 |
| 210967_x_at | calcium channel, voltage-dependent, beta 1 subunit | CACNB1 |
| 211087_x_at | mitogen-activated protein kinase 14 | MAPK14 |
| 211230_s_at | phosphoinositide-3-kinase, catalytic, delta polypeptide | PIK3CD |
| 211314_at | calcium channel, voltage-dependent, T type, alpha 1G subunit | CACNA1G |
| 211315_s_at | calcium channel, voltage-dependent, T type, alpha 1G subunit | CACNA1G |
| 211453_s_at | v-akt murine thymoma viral oncogene homolog 2 | AKT2 |
| 211483_x_at | calcium/calmodulin-dependent protein kinase (CaM kinase) II beta | CAMK2B |
| 211499_s_at | mitogen-activated protein kinase 11 | MAPK11 |
| 211500_at | mitogen-activated protein kinase 11 | MAPK11 |
| 211561_x_at | mitogen-activated protein kinase 14 | MAPK14 |
| 211580_s_at | phosphoinositide-3-kinase, regulatory subunit 3 (p55, gamma) | PIK3R3 |
| 211592_s_at | calcium channel, voltage-dependent, L type, alpha 1C subunit | CACNA1C |
| 211602_s_at | transient receptor potential cation channel, subfamily C, member 1 | TRPC1 |
| 211665_s_at | son of sevenless homolog 2 (Drosophila) | SOS2 |
| 211802_x_at | calcium channel, voltage-dependent, T type, alpha 1G subunit | CACNA1G |
| 211830_s_at | calcium channel, voltage-dependent, T type, alpha 1I subunit | CACNA1I |
| 211858_x_at | GNAS complex locus | GNAS |
| 211984_at | calmodulin 1 (phosphorylase kinase, delta) | CALM1 |
| 211985_s_at | calmodulin 1 (phosphorylase kinase, delta) | CALM1 |
| 212046_x_at | mitogen-activated protein kinase 3 | MAPK3 |
| 212239_at | phosphoinositide-3-kinase, regulatory subunit 1 (p85 alpha) | PIK3R1 |
| 212240_s_at | phosphoinositide-3-kinase, regulatory subunit 1 (p85 alpha) | PIK3R1 |
| 212249_at | phosphoinositide-3-kinase, regulatory subunit 1 (p85 alpha) | PIK3R1 |
| 212271_at | mitogen-activated protein kinase 1 | MAPK1 |
| 212273_x_at | GNAS complex locus | GNAS |
| 212555_at | protein kinase, cAMP-dependent, regulatory, type I, beta | PRKAR1B |
| 212559_at | protein kinase, cAMP-dependent, regulatory, type I, beta | PRKAR1B |
| 212607_at | v-akt murine thymoma viral oncogene homolog 3 (protein kinase B, gamma) | AKT3 |
| 212609_s_at | V-akt murine thymoma viral oncogene homolog 3 (protein kinase B, gamma) | AKT3 |
| 212669_at | calcium/calmodulin-dependent protein kinase (CaM kinase) II gamma | CAMK2G |
| 212688_at | phosphoinositide-3-kinase, catalytic, beta polypeptide | PIK3CB |
| 212757_s_at | calcium/calmodulin-dependent protein kinase (CaM kinase) II gamma | CAMK2G |
| 212777_at | son of sevenless homolog 1 (Drosophila) | SOS1 |
| 212780_at | son of sevenless homolog 1 (Drosophila) | SOS1 |
| 212912_at | ribosomal protein S6 kinase, 90 kDa, polypeptide 2 | RPS6KA2 |
| 212983_at | v-Ha-ras Harvey rat sarcoma viral oncogene homolog | HRAS |
| 213052_at | Protein kinase, cAMP-dependent, regulatory, type II, alpha | PRKAR2A |
| 213093_at | protein kinase C, alpha | PRKCA |
| 213108_at | calcium/calmodulin-dependent protein kinase (CaM kinase) II alpha | CAMK2A |
| 213245_at | adenylate cyclase 1 (brain) | ADCY1 |
| 213276_at | Calcium/calmodulin-dependent protein kinase (CaM kinase) II beta | CAMK2B |
| 213688_at | calmodulin 1 (phosphorylase kinase, delta) | CALM1 |
| 213710_s_at | Calmodulin 1 (phosphorylase kinase, delta) | CALM1 |
| 213714_at | calcium channel, voltage-dependent, beta 2 subunit | CACNB2 |
| 214019_at | — | — |
| 214157_at | GNAS complex locus | GNAS |
| 214322_at | calcium/calmodulin-dependent protein kinase (CaM kinase) II gamma | CAMK2G |
| 214495_at | calcium channel, voltage-dependent, gamma subunit 2 | CACNG2 |
| 214513_s_at | cAMP responsive element binding protein 1 | CREB1 |
| 214548_x_at | GNAS complex locus | GNAS |
| 214652_at | dopamine receptor D1 | DRD1 |
| 214824_at | — | — |
| 214853_s_at | SHC (Src homology 2 domain containing) transforming protein 1 | SHC1 |
| 214933_at | calcium channel, voltage-dependent, P/Q type, alpha 1A subunit | CACNA1A |
| 215075_s_at | growth factor receptor-bound protein 2 | GRB2 |
| 215194_at | protein kinase C, alpha | PRKCA |
| 215195_at | protein kinase C, alpha | PRKCA |
| 215340_at | adenylate cyclase 1 (brain) | ADCY1 |
| 215348_at | adenylate cyclase 1 (brain) | ADCY1 |
| 215365_at | calcium channel, voltage-dependent, beta 2 subunit | CACNB2 |
| 216098_s_at | 5-hydroxytryptamine (serotonin) receptor 7 (adenylate cyclase-coupled) /// 5-hydroxytryptamine (serotonin) receptor 7 pseudogene | HTR7 /// HTR7P |
| 216234_s_at | protein kinase, cAMP-dependent, catalytic, alpha /// similar to protein kinase, cAMP-dependent, catalytic, gamma | LOC730418 /// PRKACA |
| 216939_s_at | 5-hydroxytryptamine (serotonin) receptor 4 | HTR4 |
| 217048_at | — | — |
| 217057_s_at | GNAS complex locus | GNAS |
| 217058_at | GNAS complex locus | GNAS |
| 217303_s_at | adrenergic, beta-3-, receptor | ADRB3 |
| 217515_s_at | calcium channel, voltage-dependent, L type, alpha 1S subunit | CACNA1S |

TABLE 3-continued

CREB transcription control

| Probe Set ID | Gene Description | Gene Symbol |
|---|---|---|
| 217575_s_at | Son of sevenless homolog 2 (*Drosophila*) | SOS2 |
| 217576_x_at | son of sevenless homolog 2 (*Drosophila*) | SOS2 |
| 217620_s_at | phosphoinositide-3-kinase, catalytic, beta polypeptide | PIK3CB |
| 217644_s_at | son of sevenless homolog 2 (*Drosophila*) | SOS2 |
| 217673_x_at | GNAS complex locus | GNAS |
| 219393_s_at | v-akt murine thymoma viral oncogene homolog 3 (protein kinase B, gamma) | AKT3 |
| 219714_s_at | calcium channel, voltage-dependent, alpha 2/delta 3 subunit | CACNA2D3 |
| 220805_at | histamine receptor H2 | HRH2 |
| 221244_s_at | — | — |
| 221401_at | calcium channel, voltage-dependent, gamma subunit 5 | CACNG5 |
| 221585_at | calcium channel, voltage-dependent, gamma subunit 4 | CACNG4 |
| 221631_at | calcium channel, voltage-dependent, T type, alpha 1I subunit | CACNA1I |
| 222880_at | v-akt murine thymoma viral oncogene homolog 3 (protein kinase B, gamma) | AKT3 |
| 222960_at | calcium channel, voltage-dependent, T type, alpha 1H subunit | CACNA1H |
| 223049_at | growth factor receptor-bound protein 2 | GRB2 |
| 224137_at | calcium channel, voltage-dependent, gamma subunit 7 | CACNG7 |
| 224229_s_at | v-akt murine thymoma viral oncogene homolog 3 (protein kinase B, gamma) | AKT3 |
| 224291_at | calcium channel, voltage-dependent, gamma subunit 6 | CACNG6 |
| 224620_at | Mitogen-activated protein kinase 1 | MAPK1 |
| 224621_at | mitogen-activated protein kinase 1 | MAPK1 |
| 224986_s_at | 3-phosphoinositide dependent protein kinase-1 | PDPK1 |
| 224994_at | calcium/calmodulin-dependent protein kinase (CaM kinase) II delta | CAMK2D |
| 225000_at | Protein kinase, cAMP-dependent, regulatory, type II, alpha | PRKAR2A |
| 225011_at | Protein kinase, cAMP-dependent, regulatory, type II, alpha | PRKAR2A |
| 225019_at | calcium/calmodulin-dependent protein kinase (CaM kinase) II delta | CAMK2D |
| 225330_at | insulin-like growth factor 1 receptor | IGF1R |
| 225471_s_at | v-akt murine thymoma viral oncogene homolog 2 | AKT2 |
| 226156_at | v-akt murine thymoma viral oncogene homolog 2 | AKT2 |
| 226335_at | ribosomal protein S6 kinase, 90 kDa, polypeptide 3 | RPS6KA3 |
| 227817_at | Protein kinase C, beta 1 | PRKCB1 |
| 227824_at | Protein kinase C, beta 1 | PRKCB1 |
| 228173_at | — | — |
| 228222_at | Protein phosphatase 1, catalytic subunit, beta isoform | PPP1CB |
| 228269_x_at | Kv channel interacting protein 3, calsenilin | KCNIP3 |
| 228555_at | Calcium/calmodulin-dependent protein kinase (CaM kinase) II delta | CAMK2D |
| 228572_at | growth factor receptor-bound protein 2 | GRB2 |
| 228795_at | Protein kinase C, beta 1 | PRKCB1 |
| 229029_at | Transcribed locus | — |
| 229274_at | GNAS complex locus | GNAS |
| 229309_at | adrenergic, beta-1-, receptor | ADRB1 |
| 229392_s_at | Phosphoinositide-3-kinase, regulatory subunit 2 (p85 beta) | PIK3R2 |
| 229847_at | Mitogen-activated protein kinase 1 | MAPK1 |
| 230337_at | son of sevenless homolog 1 (*Drosophila*) | SOS1 |
| 230437_s_at | Protein kinase C, beta 1 | PRKCB1 |
| 230544_at | Ribosomal protein S6 kinase, 90 kDa, polypeptide 4 | RPS6KA4 |
| 230749_s_at | calcium/calmodulin-dependent protein kinase (CaM kinase) II delta | CAMK2D |
| 231042_s_at | Calcium/calmodulin-dependent protein kinase (CaM kinase) II delta | CAMK2D |
| 231737_at | calcium channel, voltage-dependent, gamma subunit 4 | CACNG4 |
| 231774_at | Kv channel interacting protein 3, calsenilin | KCNIP3 |
| 231793_s_at | calcium/calmodulin-dependent protein kinase (CaM kinase) II delta | CAMK2D |
| 231854_at | Phosphoinositide-3-kinase, catalytic, alpha polypeptide | PIK3CA |
| 232062_at | adenylate cyclase 1 (brain) | ADCY1 |
| 233688_at | Kv channel interacting protein 3, calsenilin | KCNIP3 |
| 234198_at | Kv channel interacting protein 3, calsenilin | KCNIP3 |
| 234647_at | Kv channel interacting protein 3, calsenilin | KCNIP3 |
| 234750_at | calcium channel, voltage-dependent, gamma subunit 8 | CACNG8 |
| 234756_at | calcium channel, voltage-dependent, gamma subunit 8 | CACNG8 |
| 235049_at | adenylate cyclase 1 (brain) | ADCY1 |
| 235780_at | protein kinase, cAMP-dependent, catalytic, beta | PRKACB |
| 235781_at | calcium channel, voltage-dependent, N type, alpha 1B subunit | CACNA1B |
| 235851_s_at | GNAS complex locus | GNAS |
| 235980_at | Phosphoinositide-3-kinase, catalytic, alpha polypeptide | PIK3CA |
| 236013_at | calcium channel, voltage-dependent, R type, alpha 1E subunit | CACNA1E |
| 236195_x_at | protein kinase C, gamma | PRKCG |
| 236281_x_at | 5-hydroxytryptamine (serotonin) receptor 7 (adenylate cyclase-coupled) | HTR7 |
| 236664_at | v-akt murine thymoma viral oncogene homolog 2 | AKT2 |
| 238636_at | calcium channel, voltage-dependent, L type, alpha 1C subunit | CACNA1C |
| 238830_at | Son of sevenless homolog 2 (*Drosophila*) | SOS2 |
| 238933_at | — | — |
| 239037_at | GNAS complex locus | GNAS |
| 240650_at | Calcium channel, voltage-dependent, R type, alpha 1E subunit | CACNA1E |
| 241619_at | calmodulin 1 (phosphorylase kinase, delta) | CALM1 |
| 241871_at | calcium/calmodulin-dependent protein kinase IV | CAMK4 |

TABLE 3-continued

CREB transcription control

| Probe Set ID | Gene Description | Gene Symbol |
| --- | --- | --- |
| 242410_s_at | calcium channel, voltage-dependent, R type, alpha 1E subunit | CACNA1E |
| 242482_at | protein kinase, cAMP-dependent, regulatory, type I, alpha (tissue specific extinguisher 1) | PRKAR1A |
| 242876_at | V-akt murine thymoma viral oncogene homolog 3 (protein kinase B, gamma) | AKT3 |
| 242973_at | calcium channel, voltage-dependent, L type, alpha 1C subunit | CACNA1C |
| 243358_at | insulin-like growth factor 1 receptor | IGF1R |
| 244256_at | Calcium channel, voltage-dependent, R type, alpha 1E subunit | CACNA1E |
| 32029_at | 3-phosphoinositide dependent protein kinase-1 | PDPK1 |
| 34726_at | calcium channel, voltage-dependent, beta 3 subunit | CACNB3 |
| 34846_at | Calcium/calmodulin-dependent protein kinase (CaM kinase) II beta | CAMK2B |
| 62987_r_at | calcium channel, voltage-dependent, gamma subunit 4 | CACNG4 |
| 214916_x_at | interferon, alpha-inducible protein 6 /// immunoglobulin heavy locus /// immunoglobulin heavy constant alpha 1 /// immunoglobulin heavy constant alpha 2 (A2m marker) /// immunoglobulin heavy constant delta /// immunoglobulin heavy constant gamma 1 (G1m marker) /// immunoglobulin heavy constant gamma 2 (G2m marker) /// immunoglobulin heavy constant gamma 3 (G3m marker) /// immunoglobulin heavy constant mu /// interleukin 8 /// sine oculis homeobox homolog 6 (*Drosophila*) /// ras-related C3 botulinum toxin substrate 1 (rho family, small GTP binding protein Rac1) /// exocyst complex component 7 /// immunoglobulin heavy variable 4-31 /// zinc finger, CW type with PWWP domain 2 | EXOC7 /// IFI6 /// IGH@ /// IGHA1 /// IGHA2 /// IGHD /// IGHG1 /// IGHG2 /// IGHG3 /// IGHM /// IGHV4-31 /// IL8 /// RAC1 /// SIX6 /// ZCWPW2 |

REFERENCES

Ait-Si-Ali S, Ramirez S, Barre F X, Dkhissi F, Magnaghi-Jaulin L, Girault J A, Robin P, Knibiehler M, Pritchard L L, Ducommun B, Trouche D, Harel-Bellan A. Histone acetyltransferase activity of CBP is controlled by cycle-dependent kinases and oncoprotein E1A. *Nature* 1998; 396:184-6.

Bannister A J, Kouzarides T. The CBP co-activator is a histone acetyltransferase. *Nature* 1996; 384:641-3.

Bolstad B M, Irizarry R A, Astrand M, Speed T P (2003) A comparison of normalization methods for high density oligonucleotide array data based on variance and bias. *Bioinformatics* 19: 185-93.

Bonni A, Brunet A, West A E, Datta S R, Takasu M A, Greenberg M E. Cell survival promoted by the Ras-MAPK signaling pathway by transcription-dependent and -independent mechanisms. *Science* 1999; 286:1358-62.

Boren T, Xiong Y, Hakam A, Wenham R, Apte S, Chan G, Kamath S G, Chen D T, Dressman H, Lancaster J M (2009) MicroRNAs and their target messenger RNAs associated with ovarian cancer response to chemotherapy. *Gynecol Oncol* 113: 249-55.

Chattopadhyay A, Chiang C W, Yang E. BAD/BCL-[X(L)] heterodimerization leads to bypass of G0/G1 arrest. *Oncogene* 2001; 20:4507-18.

Chen D T, Nasir A, Culhane A, Venkataramu C, Fulp W, Rubio R, Wang T, Agrawal D, McCarthy S M, Gruidl M, Bloom G, Anderson T, White J, Quackenbush J, Yeatman T Proliferative genes dominate malignancy-risk gene signature in histologically-normal breast tissue. *Breast Cancer Res Treat* 119: 335-46.

Danial N N. BAD: undertaker by night, candyman by day. *Oncogene* 2008; 27 Suppl 1:S53-70.

Datta S R, Dudek H, Tao X, Masters S, Fu H, Gotoh Y, Greenberg M E. Akt phosphorylation of BAD couples survival signals to the cell-intrinsic death machinery. *Cell* 1997; 91:231-41.

Datta S R, Katsov A, Hu L, Petros A, Fesik S W, Yaffe M B, Greenberg M E. 14-3-3 proteins and survival kinases cooperate to inactivate BAD by BH3 domain phosphorylation. *Mol Cell* 2000; 6:41-51.

del Peso L, Gonzalez-Garcia M, Page C, Herrera R, Nunez G. Interleukin-3-induced phosphorylation of BAD through the protein kinase Akt. *Science* 1997; 278:687-9.

Dressman H K, Berchuck A, Chan G, Zhai J, Bild A, Sayer R, Cragun J, Clarke J, Whitaker R S, Li L, Gray J, Marks J, Ginsburg G S, Potti A, West M, Nevins J R, Lancaster J M (2007) An integrated genomic-based approach to individualized treatment of patients with advanced-stage ovarian cancer. *J Clin Oncol* 25: 517-25.

Dressman H K, Berchuck A, Chan G, Zhai J, Bild A, Sayer R, Cragun J, Clarke J, Whitaker R S, Li L, Gray J, Marks J, et al. An integrated genomic-based approach to individualized treatment of patients with advanced-stage ovarian cancer. *J Clin Oncol* 2007; 25:517-25.

du Bois A, Lück H-J, Meier W, Adams H-P, Möbus V, Costa S, Bauknecht T, Richter B, Warm M, Schröder W, Olbricht S, Nitz U, et al. A randomized clinical trial of cisplatin/paclitaxel versus carboplatin/paclitaxel as first-line treatment of ovarian cancer. *J Natl Cancer Inst* 2003; 95:1320-9.

Etemadmoghadam D, deFazio A, Beroukhim R, Mermel C, George J, Getz G, Tothill R, Okamoto A, Raeder M B, Harnett P, Lade S, Akslen L A, et al. Integrated genome-wide DNA copy number and expression analysis identifies distinct mechanisms of primary chemoresistance in ovarian carcinomas. *Clin Cancer Res* 2009; 15:1417-27.

Fernando R, Foster J S, Bible A, Strom A, Pestell R G, Rao M, Saxton A, Baek S J, Yamaguchi K, Donnell R, Cekanova M, Wimalasena J. Breast cancer cell proliferation is inhibited by BAD: regulation of cyclin D1. *J Biol Chem* 2007; 282:28864-73.

Gao D, Inuzuka H, Tseng A, Chin R Y, Toker A, Wei W. Phosphorylation by Akt1 promotes cytoplasmic localization of Skp2 and impairs APCCdh1-mediated Skp2 destruction. *Nat Cell Biol* 2009; 11:397-408.

Garcia-Higuera I, Manchado E, Dubus P, Canamero M, Mendez J, Moreno S, Malumbres M. Genomic stability and tumour suppression by the APC/C cofactor Cdh1. *Nat Cell Biol* 2008; 10:802-11.

Gonzalez G A, Montminy M R. Cyclic AMP stimulates somatostatin gene transcription by phosphorylation of CREB at serine 133. *Cell* 1989; 59:675-80.

Hajra K M, Tan L, Liu J R. Defective apoptosis underlies chemoresistance in ovarian cancer. *Adv Exp Med Biol* 2008; 622:197-208.

Hanahan D, Weinberg R A. Hallmarks of cancer: the next generation. *Cell* 2011; 144:646-74.

Harada H, Andersen J S, Mann M, Terada N, Korsmeyer S J. p70S6 kinase signals cell survival as well as growth, inactivating the pro-apoptotic molecule BAD. *Proc Natl Acad Sci USA* 2001; 98:9666-70.

Herrin V E, Thigpen J T. Chemotherapy for ovarian cancer: current concepts. *Semin Surg Oncol* 1999; 17:181-8.

Holmgreen S P, Huang D C, Adams J M, Cory S. Survival activity of Bcl-2 homologs Bcl-w and A1 only partially correlates with their ability to bind pro-apoptotic family members. *Cell Death Differ* 1999; 6:525-32.

Irizarry R A, Hobbs B, Collin F, Beazer-Barclay Y D, Antonellis K J, Scherf U, Speed T P (2003) Exploration, normalization, and summaries of high density oligonucleotide array probe level data. *Biostatistics* 4: 249-64.

Iyer N G, Ozdag H, Caldas C. p300/CBP and cancer. *Oncogene* 2004; 23:4225-31.

Jemal A, Siegel R, Xu J, Ward E. Cancer statistics, 2010. *CA Cancer J Clin* 2010; 60:277-300.

Jia L, Macey M G, Yin Y, Newland A C, Kelsey S M. Subcellular distribution and redistribution of Bcl-2 family proteins in human leukemia cells undergoing apoptosis. *Blood* 1999; 93:2353-9.

Konishi Y, Lehtinen M, Donovan N, Bonni A. Cdc2 phosphorylation of BAD links the cell cycle to the cell death machinery. *Mol Cell* 2002; 9:1005-16.

Lappano R, Maggiolini M. G protein-coupled receptors: novel targets for drug discovery in cancer. *Nat Rev Drug Discov* 2011; 10:47-60.

Lee J W, Soung Y H, Kim S Y, Nam S W, Kim C J, Cho Y G, Lee J H, Kim H S, Park W S, Kim S H, Lee J Y, Yoo N J, et al. Inactivating mutations of proapoptotic Bad gene in human colon cancers. *Carcinogenesis* 2004; 25:1371-6.

Lizcano J M, Morrice N, Cohen P. Regulation of BAD by cAMP-dependent protein kinase is mediated via phosphorylation of a novel site, Ser155. *Biochem J* 2000; 349:547-57.

Marchion D C, Cottrill H M, Xiong Y, Chen N, Bicaku E, Fulp W J, Bansal N, Chon H S, Stickles X B, Kamath S G, Hakam A, Li L, et al. BAD phosphorylation determines ovarian cancer chemo-sensitivity and patient survival. *Clin Cancer Res* 2011; 17:6365-66.

Mayr B, Montminy M. Transcriptional regulation by the phosphorylation-dependent factor CREB. *Nat Rev Mol Cell Biol* 2001; 2:599-609.

McGuire W P, Hoskins W J, Brady M F, Kucera P R, Partridge E E, Look K Y, Clarke-Pearson D L, Davidson M. Cyclophosphamide and cisplatin compared with paclitaxel and cisplatin in patients with stage III and stage 1V ovarian cancer. *N Engl J Med* 1996; 334:1-6.

Miller A B, Hoogstraten B, Staquet M, Winkler A (1981) Reporting results of cancer treatment. *Cancer* 47: 207-14.

Montopoli M, Bellanda M, Lonardoni F, Ragazzi E, Dorigo P, Froldi G, Mammi S, Caparrotta L. "Metabolic reprogramming" in ovarian cancer cells resistant to cisplatin. *Curr Cancer Drug Targets* 2011; 11:226-35.

Nakayama K I, Nakayama K. Ubiquitin ligases: cell-cycle control and cancer. *Nat Rev Cancer* 2006; 6:369-81.

Neijt J P, Engelholm S A, Tuxen M K, Sorensen P G, Hansen M, Sessa C, de Swart C A, Hirsch F R, Lund B, van Houwelingen H C. Exploratory phase III study of paclitaxel and cisplatin versus paclitaxel and carboplatin in advanced ovarian cancer. *J Clin Oncol* 2000; 18:3084-92.

Omura G, Blessing J A, Ehrlich C E, Miller A, Yordan E, Creasman W T, Homesley H D. A randomized trial of cyclophosphamide and doxorubicin with or without cisplatin in advanced ovarian carcinoma. A Gynecologic Oncology Group Study. *Cancer* 1986; 57:1725-30.

Ozols R F, Bundy B N, Greer B E, Fowler J M, Clarke-Pearson D, Burger R A, Mannel R S, DeGeest K, Hartenbach E M, Baergen R. Phase III trial of carboplatin and paclitaxel compared with cisplatin and paclitaxel in patients with optimally resected stage III ovarian cancer: a Gynecologic Oncology Group study. *J Clin Oncol* 2003; 21:3194-200.

Parker D, Ferreri K, Nakajima T, LaMorte V J, Evans R, Koerber S C, Hoeger C, Montminy M R. Phosphorylation of CREB at Ser-133 induces complex formation with CREB-binding protein via a direct mechanism. *Mol Cell Biol* 1996; 16:694-703.

Ranger A M, Zha J, Harada H, Datta S R, Danial N N, Gilmore A P, Kutok J L, Le Beau M M, Greenberg M E, Korsmeyer S J. Bad-deficient mice develop diffuse large B cell lymphoma. *Proc Natl Acad Sci USA* 2003; 100: 9324-9.

Roy S S, Madesh M, Davies E, Antonsson B, Danial N, Hajnoczky G. Bad targets the permeability transition pore independent of Bax or Bak to switch between Ca2+-dependent cell survival and death. *Mol Cell* 2009; 33:377-88.

Rustin G J, Nelstrop A E, Bentzen S M, Piccart M J, Bertelsen K (1999) Use of tumour markers in monitoring the course of ovarian cancer. *Ann Oncol* 10 Suppl 1: 21-7.

Rustin G J, Nelstrop A E, McClean P, Brady M F, McGuire W P, Hoskins W J, Mitchell H, Lambert H E (1996) Defining response of ovarian carcinoma to initial chemotherapy according to serum CA 125. *J Clin Oncol* 14: 1545-51.

Searle J S, Schollaert K L, Wilkins B J, Sanchez Y. The DNA damage checkpoint and PKA pathways converge on APC substrates and Cdc20 to regulate mitotic progression. *Nat Cell Biol* 2004; 6:138-45.

Siu Y T, Jin D Y. CREB—a real culprit in oncogenesis. *FEBS J* 2007; 274:3224-32.

Smith J J, Deane N G, Wu F, Merchant N B, Zhang B, Jiang A, et al., *Gastroenterology* 138:958-968 (2009).

Song M S, Carracedo A, Salmena L, Song S J, Egia A, Malumbres M, Pandolfi P P. Nuclear PTEN regulates the APC-CDH1 tumor-suppressive complex in a phosphatase-independent manner. *Cell* 2011; 144:187-99.

Takahashi T, Yamasaki F, Sudo T, Itamochi H, Adachi S, Tamamori-Adachi M, Ueno N T. Cyclin A-associated kinase activity is needed for paclitaxel sensitivity. *Mol Cancer Ther* 2005; 4:1039-46.

Turnell A S, Stewart G S, Grand R J, Rookes S M, Martin A, Yamano H, Elledge S J, Gallimore P H. The APC/C and CBP/p300 cooperate to regulate transcription and cell-cycle progression. *Nature* 2005; 438:690-5.

Wang Q, Moyret-Lalle C, Couzon F, Surbiguet-Clippe C, Saurin J C, Lorca T, Navarro C, Puisieux A. Alterations of anaphase-promoting complex genes in human colon cancer cells. *Oncogene* 2003; 22:1486-90.

Wilson B E, Mochon E, Boxer L M. Induction of bcl-2 expression by phosphorylated CREB proteins during B-cell activation and rescue from apoptosis. *Mol Cell Biol* 1996; 16:5546-56.

Yang E, Zha J, Jockel J, Boise L H, Thompson C B, Korsmeyer S J. Bad, a heterodimeric partner for Bcl-XL and Bcl-2, displaces Bax and promotes cell death. *Cell* 1995; 80:285-91.

Zachariae W, Schwab M, Nasmyth K, Seufert W. Control of cyclin ubiquitination by CDK-regulated binding of Hct1 to the anaphase promoting complex. *Science* 1998; 282: 1721-4.

Zha J, Harada H, Osipov K, Jockel J, Waksman G, Korsmeyer S J. BH3 domain of BAD is required for heterodimerization with BCL-XL and pro-apoptotic activity. *J Biol Chem* 1997; 272:24101-4.

Zha J, Harada H, Yang E, Jockel J, Korsmeyer S J. Serine phosphorylation of death agonist BAD in response to survival factor results in binding to 14-3-3 not BCL-X(L). *Cell* 1996; 87:619-28.

Zhang X, Odom D T, Koo S H, Conkright M D, Canettieri G, Best J, Chen H, Jenner R, Herbolsheimer E, Jacobsen E, Kadam S, Ecker J R, et al. Genome-wide analysis of cAMP-response element binding protein occupancy, phosphorylation, and target gene activation in human tissues. *Proc Natl Acad Sci USA* 2005; 102:4459-64.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a compound" includes a plurality of such compounds, reference to "the compound" is a reference to one or more compounds and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different compounds or agents does not indicate that the listed compounds and agents are obvious one to the other, nor is it an admission of equivalence or obviousness.

Every compound, gene set, etc. disclosed herein is intended to be and should be considered to be specifically disclosed herein. Further, every subgroup of such compounds, genes, etc. that can be identified within this disclosure is intended to be and should be considered to be specifically disclosed herein. As a result, it is specifically contemplated that any compound, gene set, etc., subgroup of compounds, subgroup of genes, etc. can be either specifically included for or excluded from use or included in or excluded from a list of compounds, gene set, etc. For example, as one option, a group of genes is contemplated where each gene is as described herein but is not CCNB2, NEK2 or TCP1. As another example, RAC1 and PDYN can be independently and specifically included or excluded from the gene sets and methods disclosed herein.

Those skilled in the art will recognize, or be able to ascertain using no more than routine experimentation, many equivalents to the specific embodiments of the method and compositions described herein. Such equivalents are intended to be encompassed by the following claims.

We claim:

1. A method for screening for compounds that can be used to treat ovarian cancer comprising
   (a) contacting ovarian cancer cells with a test compound;
   (b) measuring expression levels of at least 50% of the following genes of the transcription CREB pathway in the cancer cells; ADCY1, ADRB1, ADRB2, ADRB3, AKT1, AKT2, AKT3, CACNA1A, CACNA1B, CACNA1C, CACNA1D, CACNA1E, CACNA1F, CACNA1G, CACNA1H, CACNA1I, CACNA1S, CACNA2D1, CACNA2D2, CACNA2D3, CACNB1, CACNB2, CACNB3, CACNB4, CACNG1, CACNG2, CACNG3, CACNG4, CACNG5, CACNG6, CACNG7, CACNG8, CALM1, CALM2, CALM3, CAMK2A, CAMK2B, CAMK2D, CAMK2G, CAMK4, CCND1, CDO1, CREB1, DRD1, DRD5, EXOC7, GNAS, GRB2, HPD, HRAS, HRH1, HRH2, HTR4, HTR6, HTR7, HTR7P, IFI6, IGF1R, IGH@, IGHA1, IGHA2, IGHD, IGHG1, IGHG2, IGHG3, IGHM, IGHV4-31, IL8, IRS1, KCNIP3, LDHA, LOC730418, MAP2K1, MAP3K11, MAPK1, MAPK11, MAPK12, MAPK13, MAPK14, MAPK3, PDPK1, PDYN, PIK3CA, PIK3CB, PIK3CD, PIK3R1, PIK3R2, PIK3R3, PPP1CA, PPP1CB, PPP1CC, PPP2CA, PPP2CB, PRKACA, PRKACB, PRKACG, PRKAR1A, PRKAR1B, PRKAR2A, PRKAR2B, PRKCA, PRKCB1, PRKCG, RAC1, RAF1, RPS6KA1, RPS6KA2, RPS6KA3, RPS6KA4, RPS6KA5, SHC1, SIX6, SOS1, SOS2, TRPC1, TRPC3, and ZCWPW2;

(c) obtaining a CREB pathway gene expression signature score of the expression levels of the genes of the transcription CREB pathway that were measured, wherein the pathway signature score is determined by $\Sigma w_i x_i$, wherein $x_i$ represents gene i expression level and $w_i$ is the corresponding weight (loading coefficient) with $\Sigma w_i^2 = 1$, (d) selecting the test compound as a compound that can be used to treat ovarian cancer when the CREB pathway gene expression signature score is decreased from the CREB pathway gene expression signature score of the expression levels of the same genes of the transcription CREB pathway in control ovarian cancer cells cultured in the absence of the test compound; and (e) repeating steps (a), (b), (c), and (d) a plurality of times each with a different test compound.

2. A method for selecting for compounds that enhance the cytotoxic response to an active agent selected from the group consisting of cisplatin, carboplatin, paclitaxel, and combinations thereof, against a cancer cell, comprising (a) contacting cancer cells with (i) cisplatin, carboplatin, paclitaxel, or combinations thereof, and (ii) a test compound;

(b) measuring expression levels of at least 50% of the following genes of the transcription CREB pathway in the cancer cells: ADCY1, ADRB1, ADRB2, ADRB3, AKT1, AKT2, AKT3, CACNA1A, CACNA1B, CACNA1C, CACNA1D, CACNA1E, CACNA1F, CACNA1G, CACNA1H, CACNA1I, CACNA1S, CACNA2D1, CACNA2D2, CACNA2D3, CACNB1, CACNB2, CACNB3, CACNB4, CACNG1, CACNG2, CACNG3, CACNG4, CACNG5, CACNG6, CACNG7, CACNG8, CALM1, CALM2, CALM3, CAMK2A, CAMK2B, CAMK2D, CAMK2G, CAMK4, CCND1, CDO1, CREB1, DRD1, DRD5, EXOC7, GNAS, GRB2, HPD, HRAS, HRH1, HRH2, HTR4, HTR6, HTR7, HTR7P, IFI6, IGF1R, IGH@, IGHA1, IGHA2, IGHD, IGHG1, IGHG2, IGHG3, IGHM, IGHV4-31, IL8, IRS1, KCNIP3, LDHA, LOC730418, MAP2K1, MAP3K11, MAPK1, MAPK11, MAPK12, MAPK13, MAPK14, MAPK3, PDPK1, PDYN, PIK3CA, PIK3CB, PIK3CD, PIK3R1, PIK3R2, PIK3R3, PPP1CA, PPP1CB, PPP1CC, PPP2CA, PPP2CB, PRKACA, PRKACB, PRKACG, PRKAR1A, PRKAR1B, PRKAR2A, PRKAR2B, PRKCA, PRKCB1, PRKCG, RAC1, RAF1, RPS6KA1, RPS6KA2, RPS6KA3, RPS6KA4, RPS6KA5, SHC1, SIX6, SOS1, SOS2, TRPC1, TRPC3, and ZCWPW2;

(c) obtaining a CREB pathway gene expression signature score of the expression levels of the genes of the transcription CREB pathway that were measured, wherein the pathway signature score is determined by $\Sigma w_i x_i$, wherein $x_i$ represents gene i expression level and $w_i$ is the corresponding weight (loading coefficient) with $\Sigma w_i^2 = 1$, (d) selecting the test compound as a compound that can be used to enhance the cytotoxic response to the active agent when the CREB pathway gene expression signature score is decreased from the CREB pathway gene expression signature score of the expression levels of the same genes of the transcription CREB pathway in control cancer cells cultured with (i) cisplatin, carboplatin, paclitaxel, or combinations thereof, but in the absence of (ii) the test compound; and (e) repeating steps (a), (b), (c), and (d) a plurality of times each with a different test compound.

* * * * *